United States Patent
Rassat et al.

(10) Patent No.: US 10,918,579 B2
(45) Date of Patent: Feb. 16, 2021

(54) DENSITY BALANCED HIGH IMPACT PERFUME MICROCAPSULES

(71) Applicant: FIRMENICH SA, Satigny (CH)

(72) Inventors: Estelle Rassat, Geneva (CH); Otto Graether, Geneva (CH); Arnaud Struillou, Geneva (CH); Glenn Verhovnik, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/471,735

(22) PCT Filed: Dec. 21, 2017

(86) PCT No.: PCT/EP2017/084032
§ 371 (c)(1),
(2) Date: Jun. 20, 2019

(87) PCT Pub. No.: WO2018/115250
PCT Pub. Date: Jun. 28, 2018

(65) Prior Publication Data
US 2020/0016049 A1  Jan. 16, 2020

(30) Foreign Application Priority Data
Dec. 22, 2016 (EP) .................................... 16206462

(51) Int. Cl.
| | | |
|---|---|---|
| *A61K 8/00* | (2006.01) | |
| *A61K 8/18* | (2006.01) | |
| *A61Q 13/00* | (2006.01) | |
| *A61K 8/11* | (2006.01) | |
| *A61K 8/65* | (2006.01) | |
| *A61K 8/81* | (2006.01) | |
| *A61K 8/87* | (2006.01) | |
| *A61K 8/88* | (2006.01) | |
| *A61Q 5/02* | (2006.01) | |
| *A61Q 19/10* | (2006.01) | |
| *C11D 3/50* | (2006.01) | |

(52) U.S. Cl.
CPC ................ *A61K 8/11* (2013.01); *A61K 8/65* (2013.01); *A61K 8/8111* (2013.01); *A61K 8/87* (2013.01); *A61K 8/88* (2013.01); *A61Q 5/02* (2013.01); *A61Q 13/00* (2013.01); *A61Q 19/10* (2013.01); *C11D 3/505* (2013.01); *A61K 2800/412* (2013.01)

(58) Field of Classification Search
CPC .......... A61Q 5/02; A61Q 13/00; A61Q 19/10; A61K 8/88; A61K 8/11; A61K 8/8111; A61K 8/84; A61K 8/65; A61K 8/87; A61K 2800/412
USPC ........................................................ 512/2, 1
See application file for complete search history.

(56) References Cited

U.S. PATENT DOCUMENTS

| 9,119,973 B2 | 9/2015 | Warr et al. |
| 2009/0035365 A1 | 2/2009 | Popplewell et al. |
| 2010/0190673 A1 | 7/2010 | Smets et al. |

FOREIGN PATENT DOCUMENTS

| CN | 104955934 A | 9/2015 | |
| EP | 2300146 B1 | 3/2017 | |
| EP | 2579976 B1 | 8/2017 | |
| EP | 2757146 B1 | 1/2018 | |
| WO | 2007004166 A1 | 1/2007 | |
| WO | WO-2011121469 A1 * | 10/2011 | ............. C11D 3/505 |
| WO | 2013068255 A1 | 5/2013 | |
| WO | 2013092375 A1 | 6/2013 | |
| WO | WO-2013092375 A1 * | 6/2013 | ............. C11D 3/505 |
| WO | 2015110568 A1 | 7/2015 | |

OTHER PUBLICATIONS

Vuilleumier et al., "Multidimensional Visualization of Physical and Perceptual Data Leading to a Creative Approach in Fragrance Development", Perfume & Flavorist, Published Sep. 2008, vol. 33, pp. 54-61.
S. Arctander, "Perfume and Flavor Chemicals", Molecules 2195-2201 and 2574-2575, Published 1969.
International Search Report for International Application No. PCT/EP2017/084032, dated Apr. 17, 2018, 3 pages.

* cited by examiner

*Primary Examiner* — Jessica Whiteley
(74) *Attorney, Agent, or Firm* — Armstrong Teasdale LLP

(57) ABSTRACT

Described herein are microcapsules having an oil-based core and a polymeric shell, where the oil-based core includes a perfume oil having high impact perfume raw materials and a density balancing material.
Perfuming compositions and consumer products including said microcapsules, in particular isotropic or structured consumer products in the form of home care or personal care products, are also described herein.

20 Claims, No Drawings

DENSITY BALANCED HIGH IMPACT PERFUME MICROCAPSULES

CROSS-REFERENCE TO RELATED APPLICATIONS

This application is a U.S. National Phase Application of PCT/EP2017/084032, filed Dec. 21, 2017, which claims the benefit of priority to European Patent Application No. 16206462.0, filed Dec. 22, 2016, the entire contents of which are hereby incorporated by reference herein.

TECHNICAL FIELD

The present invention relates to microcapsules having an oil-based core and a polymeric shell, wherein the oil-based core comprises a perfume oil having high impact perfume raw materials and a density balancing material.

Perfuming compositions and consumer products comprising said microcapsules, in particular isotropic or structured consumer products in the form of fine fragrance products, home care or personal care products, are also part of the invention.

BACKGROUND OF THE INVENTION

Microencapsulation is an efficient technology to stabilize volatile materials and to efficiently deliver such active benefit materials e.g. perfume oils onto various surfaces (fabrics, hairs . . . ) or in the air. Microcapsules, in particular those that contain an oil-based core and a polymeric shell so called core-shell, are therefore nowadays widely used in many consumer products.

One of the concerns faced by the perfumery industry is to be able to incorporate such microcapsules in various product bases (liquid detergent, fabric-conditioners, perfume boosters, dishwash, floor-cleaners, shampoo, rinse-off hair conditioner . . . ), in a cost-effectiveness way, effectiveness relating to the performance measured of the active ingredient in use, such as the olfative impact in the case of a perfume.

As a result, the perfumery industry is always looking for microcapsules with improved olfative performance.

Microcapsules have been widely described in the prior art.

One may cite for instance U.S. Pat. No. 9,119,973, US 2010/0190673, and US2009/0035365 that disclose high densified microcapsules to provide good performance in terms of stability and/or deposition. However, for example, in U.S. Pat. No. 9,119,973, microcapsules have to be used at a high dosage to deliver an effective benefit in the end-product (isotropic liquid detergent) and such a very high capsule dosage would have a very negative effect on transparency/turbidity of the end-product.

There is therefore a need for stable microcapsules which could be used in an improved cost-effectiveness way, at lower dosage but with comparable olfative impact (for example in terms of blooming effect or long-lasting effect) than capsules disclosed heretofore.

The microcapsules of the invention solve this problem as they exhibit high olfative performance in different consumer products even at a very low microcapsule dosage.

SUMMARY OF THE INVENTION

A first aspect of the present invention is therefore a microcapsule slurry comprising at least one microcapsule having an oil-based core and a polymeric shell, characterized in that the oil-based core comprises:

- 25-98 wt % of a perfume oil comprising at least 15 wt % of high impact perfume raw materials having a Log T←−4, and
- 2-75 wt % of a density balancing material having a density greater than 1.07 g/cm³.

A second object of the invention is a microcapsule powder obtained by drying the slurry as defined above.

A third object is a perfuming composition comprising
  (i) perfume microcapsules slurry as defined above or microcapsule powder as defined above;
  (ii) at least one ingredient selected from the group consisting of a perfumery carrier and a perfuming co-ingredient; and
  (iii) optionally a perfumery adjuvant.

Another object is a consumer product comprising the microcapsules slurry as defined above or a perfuming composition as defined above.

Definitions

An "isotropic base" or an "isotropic consumer product" should be understood as a liquid (including gel) that is transparent and non-structured. In other words, it is free from any structuring agent in the aqueous phase (external phase structuring) or surfactant structure (internal phase structuring).

A "structured base" or a "structured consumer product" should be understood as a liquid that is generally opaque and structured by well-known external structuring agents such as hydrogenated castor oil, structuring polymers such as polyacrylate (and copolymers), xanthan gum, tylose (hydroxyethyl cellulose) or by use of surfactants inducing internal structured like lamellar or tubular phases.

A "microcapsule", or the similar, in the present invention it is meant that capsules have a particle size distribution in the micron range (e.g. a mean diameter (d(v, 0.5)) comprised between about 1 and 1000 microns, preferably between 1 and 500 microns) and comprise an external solid oligomers-based shell or a polymeric shell and an internal continuous oil phase enclosed by the external shell.

"High impact perfume raw materials" should be understood as perfume raw materials having a LogT ←−4. The odor threshold concentration of a chemical compound is determined in part by its shape, polarity, partial charges and molecular mass. For convenience, the threshold concentration is presented as the common logarithm of the threshold concentration, i.e., Log [Threshold] ("LogT").

A "density balancing material" should be understood as a material having a density greater than 1.07 g/cm³ and having preferably low or no odor.

DETAILED DESCRIPTION OF THE INVENTION

Unless stated otherwise, percentages (%) are meant to designate percent by weight of a composition.

The present invention now has determined a way to provide stable and performing microcapsules that can be used at lower dosage level in different consumer product bases by using a specific combination between high impact perfume raw materials and high density materials.

As a result, due to the fact that those microcapsules provide an effective impact even at low dosage, they can be advantageously used notably in isotropic bases (that are, by definition, non-structured) without modifying significantly the transparency of the bases.

Indeed, up to now, microcapsules of the prior art were not suitable to be used in isotropic liquids as such bases are transparent and the required dosage of microcapsules normally used to provide a required impact would turn them turbid or opaque.

Moreover, it has been found that the microcapsules according to the invention can advantageously be suspended in a stable manner in an isotropic base without the need to add a structuring agent (that was generally mandatory to suspend capsules) thanks notably to the possibility to use them at low dosage and to the specific density of these capsules which is close to the density of the isotropic base.

It should be understood that in a microcapsule slurry, microcapsule sizes slightly differ and are defined by a narrow Gaussian distribution of particles sizes around a mean particle size. Consequently, this translates into a narrow Gaussian distribution of microcapsule densities around a mean capsule density. Then, by ensuring this mean capsule density is close to the density of the isotropic base, density of all microcapsules in the slurry is close enough to the density of the base to ensure good long-term suspension of most capsules.

Generally, surfactant-rich liquid consumer products have a density significantly above 1.00 while capsule slurries often have a mean density just below or close to 1.00. There is therefore a need to increase the average density of the capsules. As density of a capsule wall is generally higher than density of the core oil, one possibility would be to increase the proportion of capsule wall to core oil in a given capsule. However, this is olfactively counter-productive as capsules with a thicker wall are less performing (less impactful both before and after rubbing). The alternative solution of the present invention is to increase the density of the core oil by adding a proportion of density balancing material having a density greater than 1.07 to the perfume oil while at the same time enriching the said perfume oil with high impact perfume raw materials to maintain hedonic performance which would otherwise be reduced by the dilution of the perfume oil with density balancing material. The core oil thus obtained now has significantly higher density while maintaining or even exceeding the olfactive impact of the original oil.

Of course, the microcapsules of the present invention are also suitable to be used in other bases such as liquid structured consumer products or even solid consumer products since they exhibit high olfactive performance.

Thus, a first aspect of the present invention is a microcapsule slurry comprising at least one microcapsule having an oil-based core and a polymeric shell, characterized in that the oil-based core comprises:
  25-98 wt % of a perfume oil comprising at least 15 wt % of high impact perfume raw materials having a Log T←−4, and
  2-75 wt % of a density balancing material having a density greater than 1.07 g/cm$^3$.
According to a Particular Embodiment, the Oil-Based Core Comprises:
  from 25 wt % to 85 wt % of a perfume oil comprising at least 15 wt %, preferably at least 30 wt %, more preferably at least 50 wt % of high impact perfume raw materials having a Log T←−4 and
  from 15 wt % to 75 wt % of a density balancing material.
High Impact Perfume Raw Materials According to the invention, the oil-based core comprises a perfume oil comprising a certain amount of perfume raw materials with a Log T←−4.

According to a particular embodiment, the oil-based core further comprises at least one other ingredient selected from the group consisting of nutraceuticals, cosmetics, insect control agents and biocide actives.

According to another particular embodiment, the oil-based core consists of perfume raw materials.

By "perfuming raw materials" or "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

According to the invention, the oil-based core comprises 5-98% of a perfume oil comprising at least 15%, preferably at least 30%, more preferably at least 50% of high impact perfume raw materials having a Log T←−4.

The odor threshold concentration of a perfuming compound is determined by using a gas chromatograph ("GC"). Specifically, the gas chromatograph is calibrated to determine the exact volume of the perfume oil ingredient injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of the perfuming compound. To determine the threshold concentration, solutions are delivered to the sniff port at the back-calculated concentration. A panelist sniffs the GC effluent and identifies the retention time when odor is noticed. The average across all panelists determines the odor threshold concentration of the perfuming compound. The determination of odor threshold is described in more detail in C. Vuilleumier et al., Multi-dimensional Visualization of Physical and Perceptual Data Leading to a Creative Approach in Fragrance Development, Perfume & Flavorist, Vol. 33, September, 2008, pages 54-61.

According to an embodiment, the high impact perfume raw materials having a Log T←−4 are selected from the list in Table 1 below.

TABLE 1 high impact perfume raw materials having a Log T < −4
Perfume raw materials (Log T < −4)

(+−)-1-METHOXY-3-HEXANETHIOL
4-(4-HYDROXY-1-PHENYL)-2-BUTANONE
(+−)-2-(4-METHYL-3-CYCLOHEXEN-1-YL)-2-PROPANETHIOL
2-METHOXY-4-(1-PROPENYL)-1-PHENYL ACETATE
PYRAZOBUTYLE
3-PROPYLPHENOL
1-(3-METHYL-1-BENZOFURAN-2-YL)ETHANONE
2-(3-PHENYLPROPYL)PYRIDINE
1-(3,3-DIMETHYL-1-CYCLOHEXEN-1-YL)-4-PENTEN-1-ONE (A) +
1-(5,5-DIMETHYL-1-CYCLOHEXEN-1-YL)-4-PENTEN-1-ONE (B)
1-(5,5-DIMETHYL-1-CYCLOHEXEN-1-YL)-4-PENTEN-1-ONE
(3RS,3ARS,6SR,7ASR)-PERHYDRO-3,6-DIMETHYL-
BENZO[B]FURAN-2-ONE (A) + (3SR,3ARS,6SR,7ASR)-
PERHYDRO-3,6-DIMETHYL-BENZO[B]FURAN-2-ONE (B)
(+−)-1-(5-ETHYL-5-METHYL-1-CYCLOHEXEN-1-YL)-4-PENTEN-
1-ONE
(1'S,3'R)-1-METHYL-2-[(1',2',2'-
TRIMETHYLBICYCLO[3.1.0]HEX-3'-
YL)METHYL]CYCLOPROPYL}METHANOL
(+−)-3-MERCAPTOHEXYL ACETATE
(2E)-1-(2,6,6-TRIMETHYL-1,3-CYCLOHEXADIEN-1-YL)-2-
BUTEN-1-ONE
7-METHYL-2H-1,5-BENZODIOXEPIN-3(4H)-ONE
(2E,6Z)-2,6-NONADIEN-1-OL
(4Z)-4-DODECENAL
(+−)-4-HYDROXY-2,5-DIMETHYL-3(2H)-FURANONE
METHYL 2,4-DIHYDROXY-3,6-DIMETHYLBENZOATE
3-METHYLINDOLE
(+−)-PERHYDRO-4ALPHA,8ABETA-DIMETHYL-4A-
NAPHTHALENOL
PATCHOULOL
2-METHOXY-4-(1-PROPENYL)PHENOL
(+−)-5,6-DIHYDRO-4-METHYL-2-PHENYL-2H-PYRAN (A) +
TETRAHYDRO-4-METHYLENE-2-PHENYL-2H-PYRAN (B)
4-METHYLENE-2-PHENYLTETRAHYDRO-2H-PYRAN (A) +
(+−)-4-METHYL-2-PHENYL-3,6-DIHYDRO-2H-PYRAN (B)
4-HYDROXY-3-METHOXYBENZALDEHYDE
NONYLENIC ALDEHYDE
2-METHOXY-4-PROPYLPHENOL
(2Z)-3-METHYL-5-PHENYL-2-PENTENENITRILE (A) + (2E)-3-
METHYL-5-PHENYL-2-PENTENENITRILE (B)
1-(SPIRO[4.5]DEC-6-EN-7-YL)-4-PENTEN-1-ONE (A) +
1-(SPIRO[4.5]DEC-7-EN-7-YL)-4-PENTEN-1-ONE (B)
2-METHOXYNAPHTHALENE
(−)-(3AR,5AS,9AS,9BR)-3A,6,6,9A-
TETRAMETHYLDODECAHYDRONAPHTHO[2,1-B]FURAN
5-NONANOLIDE
(3AR,5AS,9AS,9BR)-3A,6,6,9A-
TETRAMETHYLDODECAHYDRONAPHTHO[2,1-B]FURAN
7-ISOPROPYL-2H,4H-1,5-BENZODIOXEPIN-3-ONE
COUMARIN
4-METHYLPHENYL ISOBUTYRATE
(2E)-1-(2,6,6-TRIMETHYL-1,3-CYCLOHEXADIEN-1-YL)-2-
BUTEN-1-ONE
BETA,2,2,3-TETRAMETHYL-DELTA-METHYLENE-3-
CYCLOPENTENE-1-BUTANOL
DELTA DAMASCONE ((2E)-1-[(1RS,2SR)-2,6,6-TRIMETHYL-3-
CYCLOHEXEN-1-YL]-2-BUTEN-1-ONE)
(+−)-3,6-DIHYDRO-4,6-DIMETHYL-2-PHENYL-2H-PYRAN
ANISALDEHYDE
PARACRESOL
3-ETHOXY-4-HYDROXYBENZALDEHYDE
METHYL 2-AMINOBENZOATE
ETHYL METHYLPHENYLGLYCIDATE
OCTALACTONE G
ETHYL 3-PHENYL-2-PROPENOATE
(−)-(2E)-2-ETHYL-4-[(1R)-2,2,3-TRIMETHYL-3-
CYCLOPENTEN-1-YL]-2-BUTEN-1-OL

TABLE 1-continued high impact perfume raw materials having a Log T < −4
Perfume raw materials (Log T < −4)

PARACRESYL ACETATE
DODECALACTONE
TRICYCLONE
(+)-(3R,5Z)-3-METHYL-5-CYCLOPENTADECEN-1-ONE
UNDECALACTONE
(1R,4R)-8-MERCAPTO-3-P-MENTHANONE
(3S,3AS,6R,7AR)-3,6-DIMETHYLHEXAHYDRO-1-BENZOFURAN-
2(3H)-ONE
BETA IONONE
(+−)-6-PENTYLTETRAHYDRO-2H-PYRAN-2-ONE
(3E,5Z)-1,3,5-UNDECATRIENE
10-UNDECENAL (A) + (9E)-9-UNDECENAL (B) +
(9Z)-9-UNDECENAL (C)
(Z)-4-DECENAL
(+−)-ETHYL 2-METHYLPENTANOATE
1,2-DIALLYLDISULFANE
(2Z)-2-TRIDECENENITRILE (A) + (3Z)-3-TRIDECENENITRILE (B) +
(3E)-3-TRIDECENENITRILE (C) + (2E)-2-TRIDECENENITRILE (D)
(+−)-2-ETHYL-4,4-DIMETHYL-1,3-OXATHIANE
(+)-(3R,5Z)-3-METHYL-5-CYCLOPENTADECEN-1-ONE
3-(4-TERT-BUTYLPHENYL)PROPANAL
ALLYL (CYCLOHEXYLOXY)ACETATE
METHYLNAPHTHYLKETONE
(+−)-(4E)-3-METHYL-4-CYCLOPENTADECEN-1-ONE (A) +
(+−)-(5E)-3-METHYL-5-CYCLOPENTADECEN-1-ONE (B) +
(+−)-(5Z)-3-METHYL-5-CYCLOPENTADECEN-1-ONE (C)
CYCLOPROPYLMETHYL (3Z)-3-HEXENOATE (A) +
CYCLOPROPYLMETHYL (3E)-3-HEXENOATE (B)
(4E)-4-METHYL-5-(4-METHYLPHENYL)-4-PENTENAL
(+−)-1-(5-PROPYL-1,3-BENZODIOXOL-2-YL)ETHANONE
4-METHYL-2-PENTYLPYRIDINE
(+−)-(E)-3-METHYL-4-(2,6,6-TRIMETHYL-2-CYCLOHEXEN-
1-YL)-3-BUTEN-2-ONE
(3ARS,5ASR,9ASR,9BRS)-3A,6,6,9A-
TETRAMETHYLDODECAHYDRONAPHTHO[2,1-B]FURAN
(2S,5R)-5-METHYL-2-(2-PROPANYL)CYCLOHEXANONE OXIME
6-HEXYLTETRAHYDRO-2H-PYRAN-2-ONE
(+−)-3-(3 -ISOPROPYL-1-PHENYL)BUTANAL
METHYL 2-((1RS,2RS)-3-OXO-2-
PENTYLCYCLOPENTYL)ACETATE (A) + METHYL 2-
((1RS,2SR)-3-OXO-2-PENTYLCYCLOPENTYL)ACETATE (B)
1-(2,6,6-TRIMETHYL-1-CYCLOHEX-2-ENYL)PENT-1-EN-3-ONE
INDOL
7-PROPYL-2H,4H-1,5-BENZODIOXEPIN-3-ONE
ETHYL PRALINE
(4-METHYLPHENOXY)ACETALDEHYDE
ETHYL TRICYCLO[5.2.1.0.(2,6)]DECANE-2-CARBOXYLATE
(+)-(1'S,2S,E)-3,3-DIMETHYL-5-(2',2',3'-
TRIMETHYL-3'-CYCLOPENTEN-1'-YL)-4-PENTEN-2-OL
(2R,4E)-3,3-DIMETHYL-5-[(1R)-2,2,3-TRIMETHYL-3-
CYCLOPENTEN-1-YL]-4-PENTEN-2-OL (A) + (2S,4E)-
3,3-DIMETHYL-5-[(1R)-2,2,3-TRIMETHYL-3-CYCLOPENTEN-
1-YL]-4-PENTEN-2-OL (B)
8-ISOPROPYL-6-METHYL-BICYCLO[2.2.2]OCT-5-ENE-2-
CARBALDEHYDE
METHYLNONYLACETALDEHYDE
4-FORMYL-2-METHOXYPHENYL 2-METHYLPROPANOATE
(E)-4-DECENAL
(+−)-2-ETHYL-4-(2,2,3-TRIMETHYL-3-CYCLOPENTEN-1-YL)-2-
BUTEN-1-OL
(1R,5R)-4,7,7-TRIMETHYL-6-THIABICYCLO[3.2.1]OCT-3-ENE (A) +
(1R,4R,5R)-4,7,7-TRIMETHYL-6-THIABICYCLO[3.2.1]OCTANE (B)
(−)-(3R)-3,7-DIMETHYL-1,6-OCTADIEN-3-OL
(E)-3-PHENYL-2-PROPENENITRILE
4-METHOXYBENZYL ACETATE
(E)-3-METHYL-5-(2,2,3-TRIMETHYL-3-CYCLOPENTEN-1-YL)-4-
PENTEN-2-OL
ALLYL (3-METHYLBUTOXY)ACETATE (A) + (+−)-ALLYL (2-
METHYLBUTOXY)ACETATE
(+−)-(2E)-1-(2,6,6-TRIMETHYL-2-CYCLOHEXEN-1-YL)-2-BUTEN-
1-ONE
(1E)-1-(2,6,6-TRIMETHYL-1-CYCLOHEXEN-1-YL)-1-PENTEN-
3-ONE

According to an embodiment, perfume raw materials having a Log T←−4 are chosen in the group consisting of aldehydes, ketones, alcohols, phenols, esters lactones, ethers, epoxydes, nitriles and mixtures thereof.

According to an embodiment, perfume raw materials having a Log T←−4 comprise at least one compound chosen in the group consisting of alcohols, phenols, esters lactones, ethers, epoxydes, nitriles and mixtures thereof, preferably in amount comprised between 20 and 70% by weight based on the total weight of the perfume raw materials having a Log T←−4.

According to an embodiment, perfume raw materials having a Log T←−4 comprise between 20 and 70% by weight of aldehydes, ketones, and mixtures thereof based on the total weight of the perfume raw materials having a Log T←−4.

According to a particular embodiment, high impact perfume raw materials comprise 4-methyl-2-pentylpyridine.

According to an embodiment, the perfume oil comprises:
4-methyl-2-pentylpyridine, and
at least one ingredient selected from the group consisting of isoeugenol, cinnamyl acetate, phenylethyl acetate, indol, dihydromyrcenol, eucalyptol, linalool, 2-ethyl-4-(2,2,3-trimethyl-3-cyclopenten-1-yl)-2-buten-1-ol, 3,3-dimethyl-5-(2,2,3-trimethyl-3-cyclopenten-1-yl)-4-penten-2-ol, [1-methyl-2-[(1',2',2'-trimethylbicyclo[3.1.0]hex-3'-yl)methyl]cyclopropyl]methynol.

The remaining perfume raw materials contained in the oil-based core have therefore a Log T>-4.

Non limiting examples of perfume raw materials having a Log T>-4 are listed in table 1A below.

TABLE 1A perfume raw materials having a Log T > −4
Perfume raw materials (Log T > −4)

ETHYL 2-METHYLBUTYRATE
(E)-3-PHENYL-2-PROPENYL ACETATE
(+−)-8-SEC-BUTYLQUINOLINE (A) + (+−)-6-SEC-BUTYLQUINOLINE
(+−)-3-(1,3-BENZODIOXOL-5-YL)-2-METHYLPROPANAL
PROPIONATE DE VERDYLE
1-(OCTAHYDRO-2,3,8,8-TETRAMETHYL-2-NAPHTALENYL)-1-ETHANONE
METHYL 2-((1RS,2RS)-3-OXO-2-PENTYLCYCLOPENTYL)ACETATE
(+−)-(E)-4-METHYL-3-DECEN-5-OL
2,4-DIMETHYL-3-CYCLOHEXENE-1-CARBALDEHYDE
1,3,3-TRIMETHYL-2-OXABICYCLO[2.2.2]OCTANE
TETRAHYDRO-4-METHYL-2-(2-METHYL-1-PROPENYL)-2H-PYRAN
ALDEHYDE C 12
1-OXA-12-CYCLOHEXADECEN-2-ONE (A) + 1-OXA-13-CYCLOHEXADECEN-2-ONE (B)
(+−)-3-(4-ISOPROPYLPHENYL)-2-METHYLPROPANAL
ALDEHYDE C 11 LENIQUE
(+−)-2,6-DIMETHYL-7-OCTEN-2-OL
(+−)-2,6-DIMETHYL-7-OCTEN-2-OL
ALLYL 3-CYCLOHEXYLPROPANOATE
(Z)-3-HEXENYL ACETATE
(2RS,5SR)-5-METHYL-2-(2-PROPANYL)CYCLOHEXANONE (A) + (2RS,5RS)-5-METHYL-2-(2-PROPANYL)CYCLOHEXANONE (B)
ALLYL HEPTANOATE
(1RS,2RS)-2-(2-METHYL-2-PROPANYL)CYCLOHEXYL ACETATE (A) + (1RS,2SR)-2-(2-METHYL-2-PROPANYL)CYCLOHEXYL ACETATE (B)
1,1-DIMETHYL-2-PHENYLETHYL

TABLE 1A-continued perfume raw materials having a Log T > −4
Perfume raw materials (Log T > −4)

BUTYRATE
GERANYL ACETATE (A) + NERYL ACETATE (B)
(+−)-1-PHENYLETHYL ACETATE
1,1-DIMETHYL-2-PHENYLETHYL ACETATE
3-METHYL-2-BUTENYL ACETATE
ETHYL 3-OXOBUTANOATE (A) <=> (2Z)-ETHYL 3-HYDROXY-2-BUTENOATE (B)
8-P-MENTHANOL
8-P-MENTHANYL ACETATE (A) + 1-P-MENTHANYL ACETATE (B)
(+−)-2-(4-METHYL-3-CYCLOHEXEN-1-YL)-2-PROPANYL ACETATE
(+−)-2-METHYLBUTYL BUTANOATE
2-{(1S)-1-[(1R)-3,3-DIMETHYLCYCLOHEXYL]ETHOXY}-2-OXOETHYL PROPIONATE
3,5,6-TRIMETHYL-3-CYCLOHEXENE-1-CARBALDEHYDE (A) + 2,4,6-TRIMETHYL-3-CYCLOHEXENE-1-CARBALDEHYDE (B)
2-CYCLOHEXYLETHYL ACETATE
ALDEHYDE C 8
ETHYL BUTANOATE
(+−)-(3E)-4-(2,6,6-TRIMETHYL-2-CYCLOHEXEN-1-YL)-3-BUTEN-2-ONE (A) + (3E)-4-(2,6,6-TRIMETHYL-1-CYCLOHEXEN-1-YL)-3-BUTEN-2-ONE (B);
1-[(1RS,6SR)-2,2,6-TRIMETHYLCYCLOHEXYL]-3-HEXANOL
1,3,3-TRIMETHYL-2-OXABICYCLO[2.2.2]OCTANE
1,3,3-TRIMETHYL-2-OXABICYCLO[2.2.2]OCTANE
ETHYL HEXANOATE
UNDECANAL
ALDEHYDE C 10
2-PHENYLETHYL ACETATE
(1S,2S,4S)-1,7,7-TRIMETHYLBICYCLO[2.2.1]HEPTAN-2-OL (A) + (1S,2R,4S)-1,7,7-TRIMETHYLBICYCLO[2.2.1]HEPTAN-2-OL (B)
(+−)-3,7-DIMETHYL-3-OCTANOL
1-METHYL-4-(2-PROPANYLIDENE)CYCLOHEXENE
(+)-(R)-4-(2-METHOXYPROPAN-2-YL)-1-METHYLCYCLOHEX-1-ENE
VERDYL ACETATE
(3R)-1-[(1R,6S)-2,2,6-TRIMETHYLCYCLOHEXYL]-3-HEXANOL (A) + (3S)-1-[(1R,6S)-2,2,6-TRIMETHYLCYCLOHEXYL]-3-HEXANOL (B) + (3R)-1-[(1S,6S)-2,2,6-TRIMETHYLCYCLOHEXYL]-3-HEXANOL (C)
(+)-(1S,1'R)-2-[1-(3',3'-DIMETHYL-1'-CYCLOHEXYL)ETHOXY]-2-METHYLPROPYL PROPANOATE

Density Balancing Material(s)

According to the invention, the oil-based core comprises 2-75 wt % of a density balancing material having a density greater than 1.07 g/cm$^3$.

The density of a component is defined as the ratio between its mass and its volume (g/cm$^3$).

Several methods are available to determine the density of a component.

One may refer for example to the ISO 298:1998 method to measure d20 densities of essential oils.

According to an embodiment, the density balancing material is chosen in the group consisting of benzyl salicylate, benzyl benzoate, cyclohexyl salicylate, benzyl phenylacetate, phenylethyl phenoxyacetate, triacetin, methyl and ethyl salicylate, benzyl cinnamate, and mixtures thereof.

According to a particular embodiment, the density balancing material is chosen in the group consisting of benzyl salicylate, benzyl benzoate, cyclohexyl salicylate and mixtures thereof.

Relative Proportion between Perfume Oil and Density Balancing Material(s)

The specific combination between high impact perfuming raw materials and density balancing material as defined in the present invention leads to an overall density of capsule close to the density of the final product.

Therefore, the relative proportion between perfume raw materials and density balancing materials can be optimized according to the density of the targeted final consumer product.

Typically, for an isotropic base having a density between 1.005 g/cm$^3$ and 1.02 g/cm$^3$, the oil-based core comprises between 60-75% of perfume oil and 25-40% of a density balancing material;

for an isotropic base having a density between 1.02 g/cm$^3$ and 1.03 g/cm$^3$, the oil-based core comprises between 50-65% of perfume oil and 35-50% of a density balancing material;

for an isotropic base having a density between 1.03 g/cm$^3$ and 1.06 g/cm$^3$, the oil-based core comprises between 35-45% of perfume oil and 55-65% of a density balancing material;

for an isotropic base having a density between 1.06 g/cm$^3$ and 1.08 g/cm$^3$, the oil-based core comprises between 25-35% of perfume oil and 65-75% of a density balancing material;

for a structured base, the oil-based core comprises between 80-95% of perfume oil and 5-20% of a density balancing material.

Microcapsules

The nature of the polymeric shell of the microcapsules of the invention can vary. As non-limiting examples, the shell can be made of a material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum arabic shell wall, and mixtures thereof.

The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

As retention of the oil core upon storage of these capsules in liquid surfactant-rich products is key, according to a particular embodiment, the core-shell microcapsules are cross-linked melamine formaldehyde microcapsules obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain a dried core-shell microcapsule;

This process is described in more details in WO 2013/092375 & WO 2015/110568, the contents of which are included by reference.

According to another embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer). According to another embodiment, the emulsifier is an anionic or amphiphilic biopolymer preferably chosen from the group consisting of polyacrylate (and copolymers especially with acrylamide), gum arabic, soy protein, gelatin, sodium caseinate and mixtures thereof According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N).

According to a particular embodiment, the polyisocyanate is a trimethylol propane-adduct of xylylene diisocyanate (commercially available from Mitsui Chemicals under the tradename Takenate® D-110N).

The preparation of an aqueous dispersion/slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo.

U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of:
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
      A) $C_4$-$C_{12}$ aromatic or aliphatic di- or tri-isocyanates and their biurets, triurets, trimmers, trimethylol propane-adduct and mixtures thereof; and/or
      B) a di- or tri-oxiran compounds of formula A-(oxiran-2-ylmethyl)$_n$ wherein n stands for 2 or 3 and l represents a $C_2$-$C_6$ group optionally comprising from 2 to 6 nitrogen and/or oxygen atoms;
   v. optionally a $C_1$-$C_4$ compounds comprising two $NH_2$ functional groups;
3) heating said dispersion;
4) cooling said dispersion.

This process is described in more details in WO 2013/068255, the content of which is included by reference.

According to another embodiment, the shell of the microcapsule is polyurea- or polyurethane-based. Examples of processes for the preparation of polyurea- and polyureathane-based microcapsule slurry are for instance described in WO2007/004166, EP 2300146, EP2579976 the contents of which is also included by reference. Typically a process for the preparation of polyurea- or polyurethane-based microcapsule slurry include the following steps:
   a) dissolving at least one polyisocyanate having at least two isocyanate groups in an oil to form an oil phase;
   b) preparing an aqueous solution of an emulsifier or colloidal stabilizer to form a water phase;
   c) adding the oil phase to the water phase to form an oil-in-water dispersion, wherein the mean droplet size is comprised between 1 and 500 µm, preferably between 5 and 50 µm;
   d) applying conditions sufficient to induce interfacial polymerisation and form microcapsules in form of a slurry.

According to the invention, it should be understood that, after encapsulation, whatever the nature of the microcapsule, the internal core of the capsule is only made of the core oil composed of a perfume oil and a high density balancing material as defined in the present invention.

Microcapsule Powder

Another object of the present invention is a microcapsule powder obtained by drying the microcapsule slurry as defined above.

According to a particular embodiment, the slurry is mixed with an emulsion of free oil in a carrier emulsion followed by a drying to obtain a hybrid microcapsule.

Any drying method known to a skilled person in the art can be used; in particular the slurry may be spray-dried preferably in the presence of a polymeric carrier material such as polyvinyl acetate, polyvinyl alcohol, dextrines, natural or modified starch, vegetable gums, pectins, xanthanes, alginates, carragenans or cellulose derivatives to provide microcapsules in a powder form.

Perfuming Composition

Another object of the present invention is a perfuming composition comprising:
   (i) perfume microcapsule slurry or microcapsule powder as defined above, wherein the oil-based core comprises a perfume;
   (ii) at least one ingredient selected from the group consisting of a perfumery carrier, a perfumery co-ingredient and mixtures thereof;
   (iii) optionally at least one perfumery adjuvant.

According to a particular embodiment, when the perfuming composition comprises a perfume microcapsule slurry, said perfuming composition can be subjected to a drying.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 30%, preferably between 0.1 and 30% by weight of microcapsule as defined above.

Consumer Products

Due to their high olfactive performance, the invention's microcapsules can advantageously be used in many application fields and used in consumer products.

Thus, microcapsules can be used in liquid form applicable to various liquid consumer products (isotropic or structured consumer products) as well as in powder form or solid, applicable to powdered or solid consumer products.

The products of the invention can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, a perfume booster, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or powder or tablet dishwashing products, toilet cleaners or products for cleaning various surfaces, for example sprays & wipes intended for the treatment/refreshment of textiles or hard surfaces (floors, tiles, stone-floors etc.), a hygiene product such as sanitary napkins, diapers, toilet paper.

Another object of the invention is a consumer product, in a liquid form, preferably in the form of a home care product, a hair care product or a body care product, said consumer product comprising the microcapsules slurry as defined above or a perfuming composition as defined above.

According to an Embodiment, the Consumer Product Comprises:
 a) from 2 to 65% by weight, relative to the total weight of the consumer product, of at least one surfactant;
 b) water and/or water-miscible hydrophilic organic solvent(s); and
 c) a microcapsule slurry as defined above, or a perfuming composition as defined above,
 d) optionally non-encapsulated perfume.

According to a particular embodiment, the consumer product is a liquid transparent isotropic consumer product, preferably in the form of a liquid detergent, a fabric-softener, a liquid perfume booster, a hair care product or a body care product.

Indeed, the invention's microcapsules have shown to be particularly suitable for isotropic consumer products since they can be used at a very low dosage and have therefore a very low impact on transparency of the final product.

According to an embodiment, said consumer product is a liquid transparent isotropic consumer product, in the form of a liquid detergent, a fabric-softener, a liquid perfume booster, a hair care product or a body care product comprising:
 a) from 2 to 65% by weight, relative to the total weight of the consumer product, of at least one surfactant;
 b) water and/or water-miscible hydrophilic organic solvent(s); and
 c) microcapsule slurry as defined above, or a perfuming composition as defined above, preferably in an amount between 0.01 and 0.3%, preferably 0.01 and 0.15%, most preferably 0.01 to 0.1% relative to the total weight of the consumer product,
 d) optionally non-encapsulated perfume.

Indeed, the invention's microcapsules have also shown to be particularly suitable for isotropic consumer products since they can be used at a very low dosage making thus having very little impact on the product turbidity and also making the final product cost-effective.

According to this embodiment, i.e. for isotropic consumer product, the oil-based core comprises between 25 and 75% of perfume oil and between 25 and 75% of density balancing material.

Typically:
 for an isotropic base having a density between 1.005 and 1.02, the oil-based core comprises between 60-75% of perfume oil and 25-40% of a density balancing material;
 for an isotropic base having a density between 1.02 and 1.03, the oil-based core comprises between 50-65% of perfume oil and 35-50% of a density balancing material;

for an isotropic base having a density between 1.03 and 1.06, the oil-based core comprises between 35-45% of perfume oil and 55-65% of a density balancing material;

for an isotropic base having a density between 1.06 and 1.08, the oil-based core comprises between 25-35% of perfume oil and 65-75% of a density balancing material.

For isotropic consumer product, perfume oil comprises preferably at least 30%, more preferably at least 50% of high impact perfume raw materials having a Log T←4 are preferred.

According to this embodiment, i.e. for isotropic consumer product, microcapsules with a mean diameter of less than 100 microns, preferably less than 50 microns and most preferably less than 25 microns are preferred as this helps suspension overtime even if particle size alone is not sufficient to ensure long-term suspension.

According to another embodiment, the consumer product is a liquid structured consumer product, preferably in the form of a liquid detergent, a fabric-conditioner, a liquid perfume booster, a shampoo, a shower gel, a liquid soap, a rinse-off hair conditioner, a body lotion.

According to an embodiment, the liquid detergent or the fabric conditioner is in the form of a low water liquid detergent or fabric conditioner unidose/pods (single or multi chambers).

Indeed, the invention's microcapsules have also shown to be particularly suitable for structured consumer products since they can be used at a very low dosage making thus the final product cost-effective.

According to another embodiment, the consumer product is a liquid structured consumer product, preferably in the form of a liquid detergent, a fabric-conditioner, a liquid perfume booster, a shampoo, a shower gel, a liquid soap, a rinse-off hair conditioner, a body lotion comprising:
  a) from 2 to 65% by weight, relative to the total weight of the consumer product, of at least one surfactant;
  b) optionally, a structuring agent, preferably in an amount between 0.05% and 8%, most preferably between 0.1% and 5% by weight;
  c) water or a water-miscible hydrophilic organic solvent; and
  d) microcapsule slurry as defined above, or a perfuming composition as defined above, preferably in an amount from 0.01% to 2.0%, preferably 0.1% and 1% by weight relative to the total weight of the consumer product, and
  e) optionally non-encapsulated perfume
is also part of the present invention.

The structuring agent is defined as any substance suitable to increase the viscosity of a fluid. One may cite for example acrylate (co)polymer & corss-linkeeds acrylate polymers, structuring gums (agar gum, xanthan gum, locust beam gums, xyloglucan, gellan gum, pectine, alginate, carageenan gum, guar and modified guars, Rhamsam gum, furcellaran gum), starch and starch derivatives, modified cellulose polymers such as methyl cellulose, hydroxyl alkyl celluloses (in particular hydroxyethyl or hydroxypropyl cellulose), hydrophobically modified hydroxyethylcellulose, modified polyethers.

According to this embodiment, i.e. for structured consumer product, the oil-based core comprises 80-95% of perfume oil and 5-20% of a density balancing material.

According to this embodiment, microcapsules with a mean diameter less than 500 microns, preferably less than 100 microns are preferred.

Another object of the present invention is a powdered or solid consumer product, preferably in the form of a powder detergent, a solid perfume booster, a dry shampoo, a soap comprising the microcapsules slurry or microcapsule powder as defined above or a perfuming composition as defined above.

A powdered or a solid consumer product, preferably in the form of a detergent, a perfume booster, a dry shampoo or a soap comprising:
  a) from 2 to 65% by weight, relative to the total weight of the consumer product, of at least one surfactant or polyethylene or polypropylene glycol(s) solid at room temperature
  b) microcapsules powder as defined above, or a perfuming composition as defined above, preferably in an amount between 0.01% and 2.0%, preferably 0.1% and 1%.
  c) optionally perfume or perfume powder that is different from the microcapsules
is also part of the present invention.

The capsules of the invention have proven to be particularly and advantageously stable in consumer products containing significant amount of surfactant.

Furthermore, despite a low dosage, they also demonstrated very good olfactive performance in different consumer products (isotropic and structured bases).

The invention will now be further described by way of examples. It will be appreciated that the invention as claimed is not intended to be limited in any way by these examples.

EXAMPLES

Synthesis of the Microcapsules According to the Invention (Capsules A and B)

| Ingredient | Capsules A [%] | Capsules B [%] |
| --- | --- | --- |
| Oil Phase | 30.9 | 30.9 |
| Perfume oil (perfume raw materials + density balancing material) | 30.28 | 30.28 |
| trimethylol propane adduct of xylylene diisocyanate[1] | 0.62 | 0.62 |
| Water phase | 69.1 | 69.1 |
| Acrylamide and acrylic acid copolymer[2] | 4.7 | 4.7 |
| Melamine-formaldehyde resins[3] | 2.45[3] | 1.25[3] |
| Water | 50.55 | 51.75 |
| Sodium hydroxide | 0.5 | 0.5 |
| Acetic acid | 0.2 | 0.2 |
| acrylamidopropyltrimonium chloride/acrylamide copolymer [4] | 10.7 | 10.7 |
| Total | 100 | 100 |
| Ratio of pure melamine/formaldehyde resins to perfume oil [5] | 0.057 | 0.029 |

[1] Takenate ® D110N (75% active solution in ethyl acetate)
[2] Alcapsol from Ciba, 20% solution in water
[3] 90/10 blend of Cymel 385 & Cymel 9370 from Cytec, both 70% solution in water
[4] Salcare SC60 from Ciba, 3% solution in water
[5] = pure melamine/formaldehyde resin (70% of quantity used in [2])/quantity of perfume oil The oil phase was prepared by admixing a polyisocyanate (trimethylol propane adduct of xylylene diisocyanate, Takenate® D-110N, origin: Mitsui Chemicals) with a core oil composed of a perfume oil (see tables 2 below) and a high density balancing material. The oil phase consisted of 2% Takenate® D-110N and 98% of core oil. After encapsulation and use of the Takenate D-110N to cross-link the melamine-formaldehyde wall, the residual level of unreacted polyisocyanate in the core oil was very low and therefore the internal core of the capsule was only made of the core oil composed of a perfume oil and a high density balancing material.

To make the capsules slurry, the acrylamide and acrylic acid copolymer and the blend of the two melamine-formaldehyde resins were dissolved in water to form the water phase. Then the perfume premix oil was added into this solution and the pH was regulated to 5 with acetic acid. The temperature was raised to 90° C. for 2 hours to allow the curing of the capsules. At this point, capsules were formed, cross-linked and stable. A 3% Salcare SC60 (acrylamidopropyltrimonium chloride/acrylamide copolymer) solution in water was then added into the mixture at 90° C. and was allowed to react for 1 hour at 90° C. Then a solution of ethylene urea (50% wt in water) was added as usually done with aminoplast capsules as an agent to scavenge residual free formaldehyde. Final slurry contains about 3% w/w of ethylene urea relative to the weight of the slurry and the mixture was left to cool down to room temperature. The final pH was adjusted to 7 with sodium hydroxide.

Synthesis of the Microcapsules According to the Invention (Capsules C)

In a round bottom flask, melamine (0.91 g), 2,2-dimethoxyethanal (60 wt % in water, 1.37 g), glyoxal (40 wt % in water, 1.73 g) and 2-oxoacetic acid (50 wt % in water, 0.58 g) were dispersed in water (1.48 g) at RT. The pH value of the dispersion was controlled with sodium hydroxide (30 wt % in water, pH=9.5). The reaction mixture was heated at 45° C. for 25 minutes to give a solution. Then water (6.31 g) was added and the resin was stirred at 45° C. for 5 min.

Resin was transferred in a 200 mL beaker. Guanazole (0.60 g) was dissolved in a solution of Ambergum 1221 (2 wt % in water, 27.04 g). The resulting solution was introduced into the beaker. An oil solution of Takenate D-110N (2.15 g) and a mix of high impact perfume and high density/low-no odour organic material (29.56 g) was added into the aqueous solution. The biphasic reaction mixture was sheared with an Ultra-turrax at 21500 rpm for 2 min. Acetic acid was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 2 h. A solution of first cationic copolymer namely acrylamidopropyltrimonium chloride/acrylamide copolymer (Salcare SC60, origin BASF) (20 g, 3 wt % in water), and second cationic copolymer such as polyquaternium-16 (Luviquat® FC550, origin BASF, Germany) (1 wt % in water), was then added and the reaction mixture was heated at 80° C. for 30 min. A solution of urea (6.25 g, 50 wt % in water) was finally added to the reaction mixture, which was heated at 80° C. for 30 min.

TABLE 2

Composition of perfume oil

| T | Perfume | | | | | Comparative | |
|---|---|---|---|---|---|---|---|
| | A[1] | B[2] | C[3] | D[4] | E[5] | F[6] | G[7] |
| T > $10^{-2}$ | 53.50% | 36% | 9% | 0% | 0% | 39% | 0% |
| $10^{-3} < T < 10^{-2}$ | 14.50% | 30.5% | 22.80% | 0% | 10% | 13% | 0% |
| $10^{-4} < T < 10^{-3}$ | 12% | 8.5% | 23.2% | 45% | 30% | 43% | 35% |
| $10^{-5} < T < 10^{-4}$ | 18.50% | 25% | 34% | 0% | 59% | 5% | 62.25% |
| T < $10^{-5}$ | 1.5% | 0% | 11% | 55% | 1% | 0% | 2.75% |
| Total | 100% | 100% | 100% | 100% | 100% | 100% | 100% |

[1] see table 2A
[2] see table 2B
[3] see table 2C
[4] see table 2D
[5] see table 2E
[6] see table 2F
[7] see table 2G

TABLE 2A

Composition of perfume A

| Ingredient Name | % | Log T |
|---|---|---|
| 1-(5,5-DIMETHYL-1-CYCLOHEXEN-1-YL)-4-PENTEN-1-ONE [1] | 0.50% | Log T < −4 |
| METHYL 2,4-DIHYDROXY-3,6-DIMETHYLBENZOATE | 0.50% | Log T < −4 |
| 2-METHOXY-4-PROPYLPHENOL | 0.50% | Log T < −4 |
| (2E)-1-[(1RS,2SR)-2,6,6-TRIMETHYL-3-CYCLOHEXEN-1-YL]-2-BUTEN-1-ONE | 1.00% | Log T < −4 |
| METHYL 2-AMINOBENZOATE | 0.50% | Log T < −4 |
| ETHYL CINNAMATE | 0.50% | Log T < −4 |
| DODECALACTONE | 0.50% | Log T < −4 |
| GAMMA UNDECALACTONE | 7.00% | Log T < −4 |
| BETA IONONE | 1.50% | Log T < −4 |
| (+−)-ETHYL 2-METHYLPENTANOATE [2] | 0.50% | Log T < −4 |
| 3-(4-TERT-BUTYLPHENYL)PROPANAL [3] | 0.50% | Log T < −4 |
| ALLYL (CYCLOHEXYLOXY)ACETATE | 0.50% | Log T < −4 |
| METHYLNAPHTYLCETONE CRIST | 0.50% | Log T < −4 |
| ETHYL TRICYCLO[5.2.1.0.(2,6)]DECANE-2-CARBOXYLATE | 0.50% | Log T < −4 |
| (+−)-2-METHYLUNDECANAL | 4.00% | Log T < −4 |
| (+−)-2-ETHYL-4-(2,2,3-TRIMETHYL-3-CYCLOPENTEN-1-YL)-2-BUTEN-1-OL [4] | 1.00% | Log T < −4 |
| ETHYL 2-METHYLBUTYRATE | 1.50% | Log T > −4 |
| CINNAMYL ACETATE | 0.50% | Log T > −4 |
| ISOBUTYLQUINOLEINE | 0.50% | Log T > −4 |
| HELIOPROPANAL 5) | 0.50% | Log T > −4 |
| VERDYL PROPIONATE | 1.50% | Log T > −4 |
| ISO E SUPER ® 6) | 3.00% | Log T > −4 |
| METHYL 2-((1RS,2RS)-3-OXO-2-PENTYLCYCLOPENTYL)ACETATE | 0.50% | Log T > −4 |
| UNDECAVERTOL | 0.50% | Log T > −4 |
| 2,4-DIMETHYL-3-CYCLOHEXENE-1-CARBALDEHYDE | 2.00% | Log T > −4 |
| EUCALYPTUS GLOBULUS | 0.50% | Log T > −4 |
| (−)-(2S,4R)-4-METHYL-2-(2-METHYL-1- | 0.50% | Log T > −4 |

TABLE 2A-continued

Composition of perfume A

| Ingredient Name | % | Log T |
|---|---|---|
| PROPEN-1-YL)TETRAHYDRO-2H-PYRAN | | |
| ALDEHYDE C 12 | 0.50% | Log T > −4 |
| 1-OXA-12-CYCLOHEXADECEN-2-ONE (A) + 1-OXA-13-CYCLOHEXADECEN-2-ONE (B) 8) | 0.50% | Log T > −4 |
| (+−)-3-(4-ISOPROPYLPHENYL)-2-METHYLPROPANAL | 7.00% | Log T > −4 |
| ALDEHYDE C 11 LENIQUE | 0.50% | Log T > −4 |
| DIHYDROMYRCENOL | 5.00% | Log T > −4 |
| PHENYLETHYL ISOBUTYRATE | 1.00% | Log T > −4 |
| ALLYL CYCLOHEXYLPROPIONATE | 0.50% | Log T > −4 |
| (Z)-3-HEXENYL ACETATE | 0.50% | Log T > −4 |
| MENTHONE | 1.00% | Log T > −4 |
| ALLYL HEPTANOATE | 6.00% | Log T > −4 |
| (1RS,2RS)-2-(2-METHYL-2-PROPANYL)CYCLOHEXYL ACETATE (A) + (1RS,2SR)-2-(2-METHYL-2-PROPANYL)CYCLOHEXYL ACETATE (B) 9) | 6.00% | Log T > −4 |
| 1,1-DIMETHYL-2-PHENYLETHYL BUTYRATE | 0.50% | Log T > −4 |
| GERANYL ACETATE | 30.00% | Log T > −4 |
| STYRALLYL ACETATE | 1.00% | Log T > −4 |
| 1,1-DIMETHYL-2-PHENYLETHYL ACETATE | 1.50% | Log T > −4 |
| PRENYL ACETATE | 0.50% | Log T > −4 |
| ETHYL ACETOACETATE | 1.00% | Log T > −4 |
| DIHYDROTERPINEOL | 1.00% | Log T > −4 |
| DIHYDROTERPENYL ACETATE | 2.00% | Log T > −4 |
| TERPENYL ACETATE EXTRA | 2.00% | Log T > −4 |
| AMYL BUTYRATE | 0.50% | Log T > −4 |
| TOTAL | 100% | |

1) Neobutenone ®, Origin: Firmenich SA, Geneva, Switzerland
2) Origin: Firmenich SA, Geneva, Switzerland
3) Bourgeonal ®, Origin: Givaudan SA, Vernier, Switzerland
4) Bactanol ®, Origin: International Flavors & Fragrances, USA
5) 3-(1,3-benzodioxol-5-yl)-2-méthylpropanal, Origin: Firmenich SA, Geneva, Switzerland
6) 1-(octahydro-2,3,8,8-tetramethyl-2-naphtalenyl)-1-ethanone Origin: International Flavors & Fragrances, USA
7) Hedione ®, Origin: Firmenich SA, Geneva, Switzerland
8) Habanolide ®, Origin: Firmenich SA, Geneva, Switzerland

TABLE 2B

Composition of perfume B

| Ingredient Name | % | Log T |
|---|---|---|
| GAMMA UNDECALACTONE | 17.00% | Log T < −4 |
| (+−)-ETHYL 2-METHYLPENTANOATE 1) | 4.00% | Log T < −4 |
| ETHYL TRICYCLO[5.2.1.0.(2,6)]DECANE-2-CARBOXYLATE | 4.00% | Log T < −4 |
| ETHYL 2-METHYLBUTYRATE E | 4.50% | LOG T > −4 |
| 2,4-DIMETHYL-3-CYCLOHEXENE-1-CARBALDEHYDE | 4.00% | LOG T > −4 |
| 2-{(1S)-1-[(1R)-3,3-DIMETHYLCYCLOHEXYL]ETHOXY}-2-OXOETHYL PROPIONATE 2) | 15.00% | LOG T > −4 |
| DIHYDROMYRCENOL | 8.00% | LOG T > −4 |
| ISOCYCLOCITRAL | 1.50% | LOG T > −4 |
| ALLYL CYCLOHEXYLPROPIONATE | 6.00% | LOG T > −4 |
| ALLYL HEPTANOATE | 14.00% | LOG T > −4 |
| 1,1-DIMETHYL-2-PHENYLETHYL BUTYRATE | 14.00% | LOG T > −4 |
| CYCLANOL ACETATE | 8.00% | LOG T > −4 |
| Total | 100.00% | |

1) Origin: Firmenich SA, Geneva, Switzerland
2) ROMANDOLIDE ®, Origin: Firmenich SA, Geneva, Switzerland

TABLE 2C

Composition of perfume C

| Ingredient Name | % | Log T |
|---|---|---|
| MENTHENETHIOL | 0.50% | Log T < −4 |
| 1-(3-METHYL-1-BENZOFURAN-2-YL)ETHANONE | 0.50% | Log T < −4 |
| CLEARWOOD ® 1) | 10.00% | Log T < −4 |
| (2E)-1-[(1RS,2SR)-2,6,6-TRIMETHYL-3-CYCLOHEXEN-1-YL]-2-BUTEN-1-ONE | 3.00% | Log T < −4 |
| ANISICALDEHYDE | 3.00% | Log T < −4 |
| BÉTA IONONE | 20.00% | Log T < −4 |
| (+−)-ETHYL 2-METHYLPENTANOATE 2) | 5.00% | Log T < −4 |
| (+−)-2-METHYLUNDECANAL | 3.00% | Log T < −4 |
| ALDEHYDE C 8 | 1.00% | Log T > −4 |
| ETHYL BUTYRATE | 0.50% | Log T > −4 |
| (+−)-(3E)-4-(2,6,6-TRIMETHYL-2-CYCLOHEXEN-1-YL)-3-BUTEN-2-ONE (A) + (3E)-4-(2,6,6-TRIMETHYL-1-CYCLOHEXEN-1-YL)-3-BUTEN-2-ONE (B); | 10.00% | Log T > −4 |
| NORLIMBANOL ® 3) | 0.50% | Log T > −4 |
| EUCALYPTOL | 10.00% | Log T > −4 |
| 1,3,3-TRIMETHYL-2-OXABICYCLO[2.2.2]OCTANE | 0.70% | Log T > −4 |
| ETHYL CAPROATE | 0.50% | Log T > −4 |
| ALDEHYDE C 11 LIQUE | 0.50% | Log T > −4 |
| ALDEHYDE C 10 | 2.00% | Log T > −4 |
| PHENYLETHYL ACETATE | 1.50% | Log T > −4 |
| (1S,2S,4S)-1,7,7-TRIMETHYLBICYCLO[2.2.1]HEPTAN-2-OL (A) + (1S,2R,4S)-1,7,7-TRIMETHYLBICYCLO[2.2.1]HEPTAN-2-OL (B) | 0.80% | Log T > −4 |
| (+−)-3,7-DIMETHYL-3-OCTANOL | 18.00% | Log T > −4 |
| 1-METHYL-4-(2-PROPANYLIDENE)CYCLOHEXENE | 3.00% | Log T > −4 |
| (+)-(R)-4-(2-METHOXYPROPAN-2-YL)-1-METHYLCYCLOHEX-1-ENE | 6.00% | Log T > −4 |
| Total | 100% | |

1) Origin: Firmenich SA, Geneva, Switzerland
2) Origin: Firmenich SA, Geneva, Switzerland
3) trans-1-(2,2,6-triméthyl-1-cyclohexyl)-3-hexanol, Origin: Firmenich SA, Geneva, Switzerland

TABLE 2D

Composition of perfume D

| | % | Log T |
|---|---|---|
| 1-(5,5-DIMETHYL-1-CYCLOHEXEN-1-YL)-4-PENTEN-1-ONE 1) | 20.00% | Log T < −4 |
| (+−)-2-ETHYL-4,4-DIMETHYL-1,3-OXATHIANE | 4.00% | Log T < −4 |
| (2E)-1-(2,6,6-TRIMETHYL-1,3-CYCLOHEXADIEN-1-YL)-2-BUTEN-1-ONE | 15% | Log T < −4 |
| ETHYLVANILLINE | 4% | Log T < −4 |
| (1'R,E)-2-ETHYL-4-(2',2',3'-TRIMETHYL-3'-CYCLOPENTEN-1'-YL)-2-BUTEN-1-OL 2) | 4% | Log T < −4 |
| ALDEHYDE SUPRA | 4% | Log T < −4 |
| CETALOX ® 3) | 2% | Log T < −4 |
| AMBROX ®DL 4) | 2% | Log T < −4 |
| EUCALYPTOL | 45.00% | Log T > −4 |
| | 100% | |

1) Neobutenone ®, Origin: Firmenich SA, Geneva, Switzerland
2) Origin: Firmenich SA, Geneva, Switzerland
3) dodecahydro-3a,6,6,9a-tetramethyl-naphtho[2,1-b]furan Origin: Firmenich SA, Geneva, Switzerland
4) (−)-(8R)-8,12-epoxy-13,14,15,16-tetranorlabdane Origin: Firmenich SA, Geneva, Switzerland

TABLE 2E

Composition of perfume E

| Ingredient Name | % | Log T |
|---|---|---|
| 1-(5,5-DIMETHYL-1-CYCLOHEXEN-1-YL)-4-PENTEN-1-ONE | 1.0% | Log T < −4 |
| 2-METHOXYNAPHTHALENE | 8.0% | Log T < −4 |
| (2E)-1-[(1RS,2SR)-2,6,6-TRIMETHYL-3-CYCLOHEXEN-1-YL]-2-BUTEN-1-ONE | 5.0% | Log T < −4 |
| ETHYL 2-METHYLBUTYRATE | 8.0% | Log T < −4 |
| GAMMA UNDECALACTONE | 15.0% | Log T < −4 |
| CYCLOPROPYLMETHYL (3Z)-3-HEXENOATE (A) + CYCLOPROPYLMETHYL (3E)-3-HEXENOATE (B) | 1.0% | Log T < −4 |
| (4E)-4-METHYL-5-(4-METHYLPHENYL)-4-PENTENAL | 5.0% | Log T < −4 |
| (+−)-1-(5-PROPYL-1,3-BENZODIOXOL-2-YL)ETHANONE | 1.0% | Log T < −4 |
| 4-METHYL-2-PENTYLPYRIDINE | 1.0% | Log T < −4 |
| (+−)-2-METHYLUNDECANAL | 15.0% | Log T < −4 |
| VERDYL ACETATE | 15.0% | Log T > −4 |
| EUCALYPTOL | 15.0% | Log T > −4 |
| (3R)-1-[(1R,6S)-2,2,6-TRIMETHYLCYCLOHEXYL]-3-HEXANOL (A) + (3S)-1-[(1R,6S)-2,2,6-TRIMETHYLCYCLOHEXYL]-3-HEXANOL (B) + (3R)-1-[(1S,6S)-2,2,6-TRIMETHYLCYCLOHEXYL]-3-HEXANOL (C) | 3.0% | Log T > −4 |
| ALLYL HEPTANOATE | 7.0% | Log T > −4 |
| Total | 100.0% | |

TABLE 2F

Composition of comparative perfume F

| | Log T | % |
|---|---|---|
| (2E)-1-(2,6,6-TRIMETHYL-1,3-CYCLOHEXADIEN-1-YL)-2-BUTEN-1-ONE | Log T < −4 | 0.50% |
| DELTA DAMASCONE | Log T < −4 | 0.50% |
| ETHYL METHYLPHENYLGLYCIDATE | Log T < −4 | 1.00% |
| DODECALACTONE CP | Log T < −4 | 0.50% |
| (+−)-ETHYL 2-METHYLPENTANOATE 1) | Log T < −4 | 2.50% |
| ETHYL 2-METHYLBUTYRATE | Log T > −4 | 2.50% |
| (1'R)-2-[2-(4'-METHYL-3'-CYCLOHEXEN-1'-YL)PROPYL]CYCLOPENTANONE 2) | Log T > −4 | 10.00% |
| VERDYL PROPIONATE | Log T > −4 | 5.00% |
| | Log T > −4 | 20.00% |
| ETHYL BUTYRATE | Log T > −4 | 0.50% |
| 2,4-DIMETHYL-3-CYCLOHEXENE-1-CARBALDEHYDE | Log T > −4 | 4.50% |
| ETHYL CAPROATE | Log T > −4 | 0.50% |
| HEXYLCINNAMIC ALDEHYDE | Log T > −4 | 9.00% |
| METHYL CINNAMATE | Log T > −4 | 0.50% |
| 2,4,6-TRIMETHYL-4-PHENYL-1,3-DIOXANE | Log T > −4 | 1.00% |
| ALLYL CYCLOHEXYLPROPIONATE | Log T > −4 | 2.50% |
| (Z)-3-HEXENYL ACETATE | Log T > −4 | 1.50% |
| (1RS,2RS)-2-(2-METHYL-2-PROPANYL)CYCLOHEXYL ACETATE (A) + (1RS,2SR)-2-(2-METHYL-2-PROPANYL)CYCLOHEXYL ACETATE (B) | Log T > −4 | 25.00% |
| BENZYLDIMETHYLCARBINOL BUTYRATE | Log T > −4 | 9.00% |
| PRENYL ACETATE | Log T > −4 | 2.00% |
| AMYL ACETATE | Log T > −4 | 0.50% |
| HEXYL ACETATE | Log T > −4 | 1.00% |

1) Origin: Firmenich SA, Geneva, Switzerland
2) Origin: Firmenich SA, Geneva, Switzerland
3) (+−)-4,6,6,7,8,8-HEXAMETHYL-1,3,4,6,7,8-HEXAHYDROCYCLOPENTA[G]ISO-CHROMENE, Origin International Flavors & Fragrances, USA
4) Verdox ™, Origin International Flavors & Fragrances, USA

TABLE 2G

Composition of perfume G

| Ingredient | Log T | % |
|---|---|---|
| NEOBUTENONE ® ALPHA[1] | Log T < −4 | 2.50% |
| (4Z)-4-DODECENAL | Log T < −4 | 0.25% |
| (2E)-1-(2,6,6-TRIMETHYL-1,3-CYCLOHEXADIEN-1-YL)-2-BUTEN-1-ONE | Log T < −4 | 2.00% |
| DELTA DAMASCONE | Log T < −4 | 6.00% |
| (Z)-6-NONENAL | Log T < −4 | 0.25% |
| UNDECALACTONE GAMMA | Log T < −4 | 8.00% |
| CYCLOPROPYLMETHYL (3Z)-3-HEXENOATE (A) + CYCLOPROPYLMETHYL (3E)-3-HEXENOATE (B) | Log T < −4 | 2.00% |
| NIRVANOL ® [2] | Log T < −4 | 4.00% |
| LINALOL BJ | Log T < −4 | 40.00% |
| ETHYL 2-METHYLBUTYRATE | Log T > −4 | 9.00% |
| HELVETOLIDE ® [3] | Log T > −4 | 9.00% |
| 2,4-DIMETHYL-3-CYCLOHEXENE-1-CARBALDEHYDE | Log T > −4 | 17.00% |
| Total | | 100.00% |

[1] 1-(5,5-dimethyl-1-cyclohexen-1-yl)-4-penten-1-one, Origin: Firmenich SA, Geneva, Switzerland
[2] (+)-(1'S,2S,E)-3,3-DIMETHYL-5-(2',2',3'-TRIMETHYL-3'-CYCLOPENTEN-1'-YL)-4-PENTEN-2-OL, Origin: Firmenich SA, Geneva, Switzerland
[3] (+)-(1S,1'R)-2-[1-(3',3'-DIMETHYL-1'-CYCLOHEXYL)ETHOXY]-2-METHYLPROPYL PROPANOATE, Origin: Firmenich SA, Geneva, Switzerland Turbidity Measurements The turbidity of the sample in NTU values was determined on a portable microprocessor turbidity meter Hanna HI 93703 by using samples of approximately 10 mL of base containing the required concentration of capsule.

Part A: Examples in an Isotropic Base

Example 1

Storage Stability of Microcapsules According to the Invention in an Isotropic Liquid Detergent d=1.025 g/cm$^3$ Protocol The stability of capsules according to the invention was studied in a liquid detergent. The model liquid detergent base used was Ultra Purex Free & Clear (d=1.025 g/cm$^3$) and was composed of water, alcohol ethoxysulfate, sodium carbonate, linear alkylbenzene sulfonate, sodium chloride, alcohol ethoxylate, sodium polyacrylate, fatty acids, disodium diaminostilbene disulfonic acid, tetrasodium edta, methylisothhiazolinone. Encapsulated perfume slurry concentration in the liquid detergent base was equivalent to 0.15%.

The amount of perfume having leaked out of the capsules was measured.

Results

Results are summarized in table 3.

TABLE 3

Perfume leakage (%) over storage

| | 22° C. | | 40° C. | |
|---|---|---|---|---|
| Perfume leakage from capsules after storage | 2 weeks | 4 weeks | 2 weeks | 4 weeks |
| Capsules A with core oil made of 57% perfume C and 43% cyclohexyl salicylate | 0.4 | 0.6 | 5.0 | 12.0 |

TABLE 3-continued

Perfume leakage (%) over storage

| Perfume leakage from capsules after storage | 22° C. | | 40° C. | |
|---|---|---|---|---|
| | 2 weeks | 4 weeks | 2 weeks | 4 weeks |
| Capsules A with core oil made of 57% perfume B and 43% cyclohexyl salicylate | 0.0 | 0.0 | 0.1 | 0.1 |

Conclusions

One can conclude that perfume leakage out of the capsules upon storage in a surfactant-rich detergent is very limited, even under highly stressed storage conditions at 40° C.

Example 2

Olfactive Performance of Microcapsules According to the Invention in an Isotropic Liquid Detergent d=1.025 g/cm³

Composition

Ultra Purex Free & Clear (d=1.025 g/cm³) composed of water, alcohol ethoxysulfate, sodium carbonate, linear alkylbenzene sulfonate, sodium chloride, alcohol ethoxylate, sodium polyacrylate, fatty acids, disodium diaminostilbene disulfonic acid, tetrasodium edta, methylisothhiazolinone.

Protocol

Fabrics (2.7 kg of cotton terry towels) were washed in a standard American vertical axis machine (MAYTAG dependable care+heavy duty 4 speed select, super capacity), using the "small-medium water level_warm_spin regular fast_normal light knits program". There were dispensed 47 g of freshly prepared liquid detergent at the start of the wash through the detergent drawer. After the wash, fabrics were either tumble dried (50 min drying in MAYTAG dependable care dryers) or line-dried overnight before the odor intensity of the cotton towels was evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor.

Results

The results are shown in table 4 below

TABLE 4

Olfactive performance of microcapsules according to the invention in Ultra Purex Free & Clear liquid detergent

| Perfume Intensity | Line Drying | | Tumble Drying | |
|---|---|---|---|---|
| | Before rubbing | After rubbing | Before rubbing | After rubbing |
| Ultra Purex Free & Clear (no capsules) | 1.89 | 2.0 | 1.48 | 1.51 |
| +0.06% capsules A with core oil made of 57% comparative Perfume F and 43% cyclohexyl salicylate | 1.94 | 2.51 | 1.55 | 1.80 |
| +0.06% capsules A with core oil made of 57% Perfume A and 43% cyclohexyl salicylate | 2.04 | 3.31 | 1.61 | 2.37 |
| +0.06% capsules A with core oil made of 57% Perfume B and 43% cyclohexyl salicylate | 2.15 | 3.90 | 1.69 | 2.91 |
| +0.06% capsules A with core oil made of 57% Perfume C and 43% cyclohexyl salicylate | 2.91 | 4.87 | 2.15 | 3.82 |
| +0.06% capsules A with core oil made of 57% Perfume D and 43% cyclohexyl salicylate | 2.95 | 5.15 | 2.10 | 4.05 |

Conclusions

After drying, both under line-drying conditions (strongest impact) & tumble drying (much tougher drying conditions), a liquid detergent comprising microcapsules according to the invention, even at a very low dosage (0.06%) show significantly better olfactive performance than a liquid detergent without any capsules or with capsules with comparative perfume F outside the invention.

One can note that the best results are obtained with microcaspules comprising a high concentration of high impact raw materials.

Furthermore, since the microcapsules can be used at a very low dosage level in the isotropic base, it does not affect significantly the transparency of the product (adding 0.06% of capsule slurry only increases the measured turbidity by about 45 NTU).

Example 3

Olfactive Performance of Microcapsules According to the Invention in an Isotropic Liquid Detergent d=1.05 g/cm³

Composition of the Isotropic Liquid Detergent Base

Persil Universal Gel (d=1.05) composed of Aqua, Alcohols, C12-14, ethoxylated, sulfates, sodium salts, Benzenesulfonic acid, C10-13-alkyl derivs. sodium salts, Alcohols, C12-18, ethoxylated, Sodium metaborate, anhydrous, enzymes Protocol (Washing Conditions)

Fabrics (2.0 kg of cotton terry towels) were washed at 40° C. in a standard European horizontal axis machine (Miele Novotronic W 900-79 CH). There were dispensed 75 g of Persil Universal Gel (Henkel Germany) isotropic liquid detergent at the start of the wash through the detergent drawer. After the wash, fabrics were line-dried overnight before the odor intensity of the cotton towels was evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor. The results are shown in table 5 below:

TABLE 5

Olfactive performance of microcapsules according to the invention in Persil Universal Gel

| Perfume Intensity | Line Drying | |
|---|---|---|
| | Before rubbing | After rubbing |
| Persil Universal Gel (Germany) (no capsules) | 2.82 | 3.10 |
| +0.05% of capsules A with core oil made of 38% | 2.95 | 3.20 |

TABLE 5-continued

Olfactive performance of microcapsules according to the invention in Persil Universal Gel

| Perfume Intensity | Line Drying | |
|---|---|---|
| | Before rubbing | After rubbing |
| comparative Perfume F and 62% cyclohexyl salicylate | | |
| +0.05% capsules A with core oil made of 38% Perfume A and 62% cyclohexyl salicylate | 3.05 | 3.50 |
| +0.05% capsules A with core oil made of 38% Perfume C and 62% cyclohexyl salicylate | 3.33 | 4.13 |
| +0.05% capsules A with core oil made of 38% Perfume D and 62% cyclohexyl salicylate | 3.30 | 4.45 |

Conclusion

The above results underline a clear capsule effect versus reference without capsules or reference with capsules with comparative perfume F outside the invention.

The most satisfactory results in terms of rubbing performance are obtained with microcapsules having a high concentration of high impact materials (even if they are used at a very low dosage in the base).

Furthermore, since the microcapsules can be used at a very low dosage level in the isotropic base, it does not affect significantly the transparency of the product (adding 0.05% of capsule slurry only increases the measured turbidity by about 35 NTU)

Example 4

Olfactive Performance of Microcapsules According to the Invention in an Isotropic Liquid Fabric Softener d=1.007 g/cm³

Composition of Vernel Soft & Oils Gold according to (EC) No 648/2004

Aqua, Propylene glycol, Polyethanaminiumester & acids methyl sulfate salt, PEG40 hydrogenated castor oil, Perfume, Isopropyl alcohol, Cationic Polyacrylate, Benzisothiazolinone, Colorant Ingredients are in decreasing order of dosage and <5%, except Aqua Wash & Rinse Protocol Cotton terry towels (20 pieces, 18 cm*18 cm, about 30 g each) were washed with 30 g of unperfumed detergent in a European washing machine (Miele Novotronic W300-33CH) at 40° C. using the short cycle program. The wash was followed by a rinse at 900 rpm with 12.7 g of Vernel Soft & Oils Gold isotropic fabric-softener (Henkel Germany). The terry towels were then line dried for 24 hours before being evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor.

Results

The results are shown in tables 6 and 7 below:

TABLE 6

Olfactive performance of microcapsules according to the invention in a commercial fabric softener (Vernel Soft & Oils Gold)

| Perfume Intensity | Line Drying | |
|---|---|---|
| | Before rubbing | After rubbing |
| Vernel Soft & Oils Gold (Germany) (no capsules) | 1.80 | 2.23 |
| +0.03% of capsules A with core oil made of 67% of comparative Perfume F and 33% cyclohexyl salicylate | 1.90 | 2.55 |
| +0.03% capsules A with core oil made of 67% Perfume A and 33% cyclohexyl salicylate | 2.07 | 3.31 |
| +0.03% capsules A with core oil made of 67% Perfume C and 33% cyclohexyl salicylate | 2.36 | 4.01 |
| +0.03% capsules A with core oil made of 67% Perfume D and 33% cyclohexyl salicylate | 2.40 | 4.60 |

Conclusion

The above results underline a clear capsule effect versus reference without capsules.

Furthermore, results in terms of rubbing performance for the capsules according to the invention are better when compared to the base comprising capsules outside of the invention.

The most satisfactory results in terms of rubbing performance are obtained with microcapsules having a high concentration of high impact materials (even if they are used at a very low dosage in the base).

Furthermore, since the microcapsules can be used at a very low dosage level in the isotropic base, it does not affect significantly the transparency of the product (adding 0.03% of capsule slurry only increases the measured turbidity by about 25 NTU).

TABLE 7

Olfactive performance of microcapsules according to the invention in a fabric softener (Vernel Soft & Oils Gold)

| Perfume Intensity | Line Drying | |
|---|---|---|
| | Before rubbing | After rubbing |
| Vernel Soft & Oils Gold (Germany) (no capsules) | 1.80 | 2.23 |
| +0.03% of capsules B with core oil made 67% comparative Perfume F and 33% benzyl benzoate | 1.90 | 2.50 |
| +0.03% capsules B with core oil made of 67% Perfume A and 33% benzyl benzoate | 2.12 | 3.02 |
| +0.03% capsules B with core oil made of 67% Perfume C and 33% benzyl benzoate | 2.69 | 4.17 |
| +0.03% capsules B with core oil made of 67% Perfume D and 33% benzyl benzoate | 2.8 | 4.80 |

Conclusion

Results in terms of rubbing performance for the capsules according to the invention are better when compared to the base comprising capsules outside of the invention.

Furthermore, microcapsules can be used at a very low dosage level in the isotropic base. So, it does not affect significantly the transparency of the product (adding the 0.03% of capsule slurry only increases the measured turbidity by about 25 NTU).

Example 5

Olfactive Performance of Microcapsules According to the Invention in an Isotropic Liquid Fabric Softener d=1.02 g/cm³

Composition of Excelia Isotropic Fabric-Softener (Based on MSDS)

Aqua, 1—<5% nonionics surfactants, 1—<5% diquaternary Polydimethylsiloxane, 0.1—<1% Hydroxypropyl Methylcellulose, Perfume, Benzisothiazolinone, Methylisothiazolinone.

Wash and Rinse Protocol

Cotton terry towels (20 pieces, 18 cm*18 cm, about 30 g each) were washed with 30 g of unperfumed detergent in a European washing machine (Miele Novotronic W300-33CH) at 40° C. using the short cycle program. The wash was followed by a rinse at 900 rpm with 12.7 g of Exelia isotropic fabric-softener (Migros Switzerland). The terry towels were then line dried for 24 hours before being evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor.

Results

The results are shown in table 8 below.

TABLE 8

Olfactive performance of microcapsules according to the invention in a fabric softener (Exelia Blue Splash)

| Perfume Intensity | Line Drying | |
|---|---|---|
| | Before rubbing | After rubbing |
| Commercial Exelia Blue Splash (Switzerland August 2016) | 2.43 | 2.66 |
| +0.05% of capsules B with core oil made of 65% comparative Perfume F and 35% benzyl salicylate | 2.50 | 3.16 |
| +0.05% capsules B with core oil made of 65% Perfume C and 35% benzyl salicylate | 2.68 | 4.36 |
| +0.05% capsules B with core oil made of 65% Perfume D and 35% benzyl salicylate | 2.71 | 5.08 |
| +0.05% capsules B with core oil made of 65% Perfume E and 35% benzyl salicylate | 3.20 | 5.17 |

Conclusion

After drying, fabrics which have been washed and conditioned with microcapsules according to the invention even at a very low dosage (0.05%) deliver a very strong rubbing effect.

Furthermore, since the microcapsules can be used at a very low dosage level in the isotropic base, it does not affect significantly the transparency of the product (adding 0.05% of capsule slurry only increases the measured turbidity by about 40 NTU).

Example 6

Olfactive Performance of Microcapsules According to the Invention in an Isotropic Liquid Shampoo d=1.03 g/cm³

Composition

A model isotropic shampoo base (see table 9), was prepared to test the capsules on hair.

TABLE 9

Composition of the transparent isotropic shampoo base

| Product | Description | Concentration [wt %] |
|---|---|---|
| Water | | 44.4 |
| Ucare Polymer JR-400 | Polyquaternium-10 | 0.3 |
| Glycerin 85% | | 1.0 |
| Glydant | DMDM Hydantoin | 0.2 |
| Texapon NSO IS | Sodium Laureth Sulfate | 28.0 |
| Tego Betain F 50 | Cocamidopropyl Betaine | 3.2 |
| Amphotensid GB 2009 | Disodium Cocoamphodiacetate | 2.0 |
| Texapon NSO IS | Sodium Laureth Sulfate | 4.0 |
| Monomuls 90 L-12 | Glyceryl Laureate | 0.3 |
| Water deionised | | 1.0 |
| Nipagin Monosodium | Sodium Methylparaben | 0.1 |
| Sodium Chloride 10% aq. | | 15.0 |
| Perfume | | 0.5 |
| Total | | 100 |

Shampoo Wash Protocol a) Incorporate capsule at the required dosage in the shampoo base
b) Wet the hair swatches under warm water before applying the shampoo per hair swatch (0.1 g of product for 1 g hair)
c) Thoroughly rinse the hair swatches by dipping them 3 times into warm water before rinsing them for 30 seconds under running tap water
d) Squeeze off residual water before air-drying the hair swatches on a drying rack
e) Evaluate after 24 hours, when hair is fully dry Evaluation on Hair Fragrance intensity of the hair swatches was evaluated before combing the hair according to the following perfume intensity scale: 1—Imperceptible, 2—Slightly perceptible, 3—Weak, 4—Medium, 5—Sustained, 6—Intense, 7—Very intense. Hair swatches were combed three times with the thin part of the comb. Perfume intensity just after combing the hair was evaluated according to the same scale. Once a hair swatch was touched, rubbed or combed, it could not be evaluated again for the "before combing" step. Thus at least two sets of hair swatches were prepared. One was never combed and used only for the "before combing" step. The other set was combed by a maximum of ten panelists for the "after combing" step. If more than ten panelists were required, another set of hair swatches was prepared for the "after combing" step. Throughout the washing protocol, hands were protected by gloves.

Results

The results are shown in Table 10 below.

TABLE 10

Olfactive performance of microcapsules according to the invention in an isotropic shampoo

| Perfume Intensity | After 24 h air Drying | |
|---|---|---|
| | Before combing | After combing |
| Isotropic Shampoo (no capsules) | 1.5 | 1.85 |
| +0.02% Capsules C with core oil made of 60% Comparative Perfume F & 40% cyclohexyl salicylate | 1.9 | 2.4 |
| +0.02% Capsules C with core oil made of 70% Perfume G & 30% cyclohexyl salicylate | 2.1 | 3.6 |

TABLE 10-continued

Olfactive performance of microcapsules according to the invention in an isotropic shampoo

| Perfume Intensity | After 24 h air Drying | |
|---|---|---|
| | Before combing | After combing |
| +0.04% Capsules C with core oil made of 60% Comparative Perfume F & 40% cyclohexyl salicylate | 2.1 | 2.8 |
| +0.04% Capsules C with core oil made of 60% Perfume G & 40% cyclohexyl salicylate | 2.3 | 3.9 |
| +0.07% Capsules C with core oil made of 60% Comparative Perfume F & 40% cyclohexyl salicylate | 2.3 | 3.6 |
| +0.07% Capsules C with core oil made of 60% Perfume G & 40% cyclohexyl salicylate | 2.6 | 4.2 |

Conclusions

All hair swatches washed and conditioned with capsules according to the invention do deliver a perfume boost even for a very low dosage.

This can be achieved with only 0.02% of capsules C loaded with the high impact perfume G but requires a much higher dosage of 0.07% of capsules with comparative perfume F outside the invention.

Example 11

Olfactive Performance of Microcapsules A Containing Perfume D According to the Invention at 0.1% in an Isotropic Unit Dose/Pods d=1.0579 g/cm$^3$ Composition Low water liquid detergent composition for unidose pods) composed of C12-15 pareth 7, MEA-hydrogenated cocoate, MEA-dodecylbenzene sulfonate, propylene glycol, glycerine water, polyvinyl alcohol, polypropylene terephthalate polyoxyoethylene terephthalate, sorbitol, sodium diethyenetriamin pentamethylene phosphonate, MEA-sulfate, potassium sulfite, ethynolamine, peptide salt, glycol, subtilisin, perfume, disodium distyrybiphenyl disulfonate, talc, amylase, sodium chloride, denatonium benzoate, disubstitued alaninamide, dye, mannanase In range term this composition contains 5-15% anionic surfactants, nonionic surfactant, soap and less than 5% enzyme optical brightener, perfume, phosphonate.

Protocol

Fabrics (2.0 kg of cotton terry towels) were washed at 40° C. in a standard European horizontal axis machine (Miele Novotronic W 900-79 CH). A pod was prepared by adding 25 g of freshly prepared liquid detergent composition above (with or without 0.1% of capsule A) into a polyvinylalcohol pouch. The pod was placed in the drum of the washing machine at the start of the wash. After the wash, fabrics were line-dried overnight before the odor intensity of the cotton towels was evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor.

Results

The results are shown in table 11 below

TABLE 11

Olfactive performance of microcapsules according to the invention in Skip Active Clean unit dose

| Perfume Intensity | Line Drying | |
|---|---|---|
| | Before rubbing | After rubbing |
| Low water liquid detergent composition in unidose pods | 2.38 | 2.87 |
| Capsule A with 0.1% with core oil made of 38% Perfume F and 62% cyclohexyl salicylate | 2.94 | 3.52 |
| Capsule A with 0.1% with core oil made of 38% Perfume D and 62% cyclohexyl salicylate | 3.43 | 4.79 |

Conclusions

After drying, a unit dose liquid detergent comprising a very low dosage (0.1%) of microcapsules A with core oil made of 38% Perfume D and 62% cyclohexyl salicylate according to the invention, is outperforming a liquid detergent unit dose without any capsules or 0.1% of capsules A containing a comparative perfume F outside the invention.

Example 12

Suspension of Microcapsules According to the Invention in Isotropic Liquid Detergents Composition Base A is composed of water, 5-15% Non-Ionic Surfactants, Anionic Surfactants. Less than 5% Soap, Phosphonate, Enzymes, Optical Brightener, Perfume Base B is a 2 in 1 liquid detergent composed of water, 5-15% Anionic surfactant, less than 5% non-ionic surfactant, cationic surfactant, soap, phosphonate, polycarboxylate, enzyme, methylisothiazolinone, perfume.

Base C is composed of water, soap base (plant origin), surfactant, chelating Agent, detergent auxiliary, perfume Base D is composed of water, sodium dodecylbenzenesulfonate, sodium laureth sulfate, C12-15 pAreth-7, sodium hydrogenated cocoate, aziridine homopolymer ethoxylated, acrylate copolymers, perfume, propylene glycol, sodium diethylenetriamine pentamethylene phosphoane, TEA-hydrogenated cocoate, TEA, 1,4 benzenedicarboxylic acid, 1,4 dimethyl ester, polymer 1, sodium sulfate, glycerin, sorbitol, benzisothiazolinone, protease, sodium hydroxide, peptides, salts, sugar from fermentation, boronic acid, amylase, cellulase, mannanase, dye In range term this composition contains 5-15% anionic surfactants and less than 5% nonionic surfactant, optical brightener, perfume, phosphonate, soap, benzisothiazolinone Base E is composed of water, 5-10% alcohol C12-18 7EO, 1-5% sodium salts of benzenesulfonic acid C10-13 alkyls derivatives, 1-5% sodium carbonate, 1-5% alcohols C12-18 7EO, 1-5% sodium chloride, Enzymes, Perfume

TABLE 12

Physical parameters of bases A-E

|        | Specific Gravity | Dry Matter % | Viscosity 5 s$^{-1}$ | Viscosity 21 s$^{-1}$ | Viscosity 106 s$^{-1}$ | Dose per wash in front loading washing machine |
|---|---|---|---|---|---|---|
| Base A | 1.016  | 25.4%  | 326  | 318  | 307  | 30 |
| Base B | 1.0344 | 19.93% | 658  | 631  | 572  | 65 |
| Base C | 1.0370 | 30.69% | 2460 | 2300 | 1890 | 30 |
| Base D | 1.0446 | 23.21% | 958  | 788  | 619  | 75 |
| Base E | 1.0616 | 18.98% | 465  | 456  | 394  | 40 |

Protocol

Capsules from the invention (with core oil made of 38% Perfume D and 62% cyclohexyl salicylate, SG=1.0346) with three different particle size batch, either 5, 10 or 25 microns, were applied @0.05% in all bases described above with various densities and viscosities. The suspension properties were monitored visually up to 2 weeks time at room temperature.

Results

Suspension of this capsule of the invention in various worldwide isotropic liquid detergent is showing promising results after 2 weeks storage at RT. As expected, as density of the core oil of these capsules of the invention is quite high at 1.0346, the best results are achieved in the higher density isotropic liquid detergent formulations (SG=1.03-1.07), more specifically in the base of higher density (base E SG=1.06) and also in the base of slightly lower density (base C SG=1.037) but with a higher viscosity profile. Even in the lower density and viscosity formulation Base A, only a slight sedimention is noticeable. By contrast, capsules only containing Perfume D separate in a matter of hours/a few days in all these bases, even in the higher viscosity bases.

Example 13

Suspension of Microcapsules According to the Invention in a Isotropic Liquid Detergent SG of 1.0351

Composition

The base is composed of water, sodium dodecylbenzenesulfonate, sodium laureth sulfate, C12-15 pAreth-7, sodium hydrogenated cocoate, aziridine homopolymer ethoxylated, acrylate copolymers, perfume, propylene glycol, sodium diethylenetriamine pentamethylene phosphoane, TEA-hydrogenated cocoate, TEA, 1,4 benzenedicarboxylic acid, 1,4 dimethyl ester, polymer 1, sodium sulfate, glycerin, sorbitol, benzisothiazolinone, protease, sodium hydroxide, peptides, salts, sugar from fermentation, boronic acid, amylase, cellulase, mannanase, dye.

Protocol

Encaps from the invention (with core oil made of 38% Perfume D and 62% cyclohexyl salicylate, SG=1.0346) were applied @ 0.05% in the base and stored in a 2 liter packaging for a period of 2 months at both room temperature and 37° C. The bottles were put on a shelf and left untouched

TABLE 13

Suspension properties

| | Capsules containing only Perfume D (SG = 0.945) | Capsules from the invention (with core oil made of 38% Perfume D and 62% cyclohexyl salicylate, SG = 1.0346) | | |
|---|---|---|---|---|
| | | Particle size | | |
| | 5, 10 or 25 microns | 5 microns | 10 microns | 25 microns |
| Base A | Fast separation, capsules float overnight | Good suspension properties with a very slight sedimentation | Medium suspension properties with a slight sedimentation | Medium suspension properties with a slight sedimentation |
| Base B | | Very good suspension with no separation visible | Good suspension with no separation visible | Good suspension with no separation visible |
| Base C | Full separation takes about a week | Very good suspension with no separation visible | Very good suspension with no separation visible | Very good suspension with no separation visible |
| Base D | Full separation takes about 3 days | Good suspension with no separation visible | Good suspension with no separation visible | Good suspension with no separation visible |
| Base E | Fast separation, capsules float overnight | Very good suspension with no separation visible | Very good suspension with no separation visible | Very good suspension with no separation visible | before being analysed. Every day, one fraction of liquid detergent (75 g per wash) was poured from the bottle, this for 27 days until the bottle is completely empty to somehow mimic what is happening at the consumer house. Some fractions were selected and analysed in order to determine whether there was a gradient in concentration within the bottle describing either a sign of creaming or sedimentation or if we still have encaps homogeneously dispersed in the product.

The amount of encapsulated oil was determined in each fraction by solvent extraction and GS/MS analysis. Turbidity measurements were also performed.

Results

Microcapsules from the invention (with core oil made of 38% Perfume D and 62% cyclohexyl salicylate) showed good suspension properties in this isotropic liquid detergent (SG of 1.0351) even after 2 months storage at either RT or 37° C. None of the fractions analysed are encaps-free. After 1 month at RT all fractions except the last one contain more or less the same amount of microcapsules, the dosages obtained being very close from the target dosage. This confirms that separation has been very limited over this one month storage. The NTU value correlates pretty well with the analytical finding.

Even an accelerated torture test of 2 month storage @ 37° C., we still detect microcapsules in each fractions analysed but at a lower concentration than was noticed at RT. Here again, difference in capsule concentration between the various fractions is relatively limited and only the last fraction seems to be clearly enriched in capsules. NTU values are also well aligned.

TABLE 14

NTU values

| Fraction | Results after 2 month RT | NTU after 2 month RT | Results after 2 month 37° C. | NTU after 2 month 37° C. |
| --- | --- | --- | --- | --- |
| Ref | 0.05% | 69 | 0.05% | 62 |
| 1 (top of the bottle) | 0.041% | 51.5 | 0.015% | 24.52 |
| 2 | 0.039% | 53 | 0.017% | 27.23 |
| 7 | 0.045% | 53.75 | 0.020% | 29.5 |
| 8 | 0.045% | 54.25 | 0.022% | 27.47 |
| 14 | 0.046% | 57 | 0.023% | 30.02 |
| 15 | 0.045% | 57 | 0.022% | 34.34 |
| 20 | 0.046% | 57.25 | 0.026% | 37.66 |
| 21 | 0.044% | 56.25 | 0.028% | 36.75 |
| 26 | 0.044% | 54 | 0.021% | 31.27 |
| 27 (bottom of the bottle) | 0.079% | 99.75 | 0.089% | 99 |

Part B: Examples in a Structured Base

Example 14

Olfactive Performance of Microcapsules According to the Invention in a Concentrated Structured Liquid Fabric Softener Composition A concentrated unperfumed fabric softener base was prepared by admixing the ingredients listed in Table 15, in the amounts indicated. The percentages are defined by weight relative to the total weight of the unperfumed fabric softener base.

TABLE 15

Formulation of the concentrated unperfumed fabric softener base (pH ~2.85)

| Ingredient | % |
| --- | --- |
| Stepantex VL90 A Diester Quat[1] | 16.50 |
| Proxel GXL[2] | 0.04 |
| CaCl$_2$ (10% aqueous solution) | 0.20 |
| Water | 83.26 |

[1]Origin: Stepan
[2]Origin: Avecia

Softeners were prepared by adding Capsules at 0.45% by weight, relative to the total weight of the softener into the unperfumed softener base of Table 11 under gentle shaking.

Wash & Rinse Protocol:

Cotton terry towels (20 pieces, 18 cm*18 cm, about 30 g each) were washed with 30 g of unperfumed detergent in a European washing machine (Miele Novotronic W300-33CH) at 40° C. using the short cycle program. The wash was followed by a rinse at 900 rpm with 12.7 g of above concentrated fabric-softener. The terry towels were then line dried for 24 hours before being evaluated by a panel of 20 trained panelists. The panelists were asked to rate the odor intensity of the towels after gentle rubbing of the fabrics by hand on a scale from 1 to 10, 1 corresponding to odorless and 10 corresponding to a very strong odor.

Results

The results are shown in table 16 below.

TABLE 16

Olfactive performance of microcapsules according to the invention in a fabric softener

| | Line Drying | |
| --- | --- | --- |
| Perfume Intensity | Before rubbing | After rubbing |
| Unperfumed fabric-softener (no capsules) | 1.85 | 2.15 |
| +0.25% of capsules B with core oil made of 90% comparative Perfume F and 10% benzyl benzoate | 2.85 | 4.55 |
| +0.25% Capsules B with core oil made of 90% Perfume A and 10% benzyl benzoate | 3.4 | 6.73 |
| +0.08% Capsules B with core oil made of 90% Perfume C and 10% benzyl benzoate | 3.75 | 6.6 |
| +0.08% Capsules B with core oil made of 90% Perfume D and 10% benzyl benzoate | 3.8 | 7.35 |

Conclusion

After drying, fabrics which have been washed and conditioned with either capsules deliver a strong perfume boost of dry fabrics. This can be achieved with only 0.08% of capsules loaded with the high impact perfumes C and D or with 0.25% of capsules of perfume A.

Example 15

Olfactive Performance of Microcapsules According to the Invention in a Concentrated Structured Liquid Detergent Composition

| Ingredients | Type of product | Supplier | % |
| --- | --- | --- | --- |
| Hostapur SAS 60 | Anionics Surfactant | Clariant | 7 |

-continued

| Ingredients | Type of product | Supplier | % |
|---|---|---|---|
| Edenor K 12-18 | Fatty Acid | Cognis | 7.5 |
| Genapol LA 070 | Nonionic Surfactant | Clariant | 17 |
| Triethanolamine | | Fluka | 7.5 |
| 1,2 Propylene Glycol | Solvent | Carlo Herba | 11 |
| Citric Acid 50% aqueous solution | Organic builder | Fluka | 6.5 |
| KOH 45% aqueous solution | Buffering agent | Carlo Herba | 9.5 |
| Aculyn 88 | Acrylates/Steareth-20 Methacrylate structuring Crosspolymer | Dow Chemical | 6 |
| Properase L | Protease Enzyme | Genencor International | 0.2 |
| Puradax EG L | Cellulase Enzyme | Genencor International | 0.2 |
| Purastar ST L | Alpha-Amylase Enzyme | Genencor International | 0.2 |
| Deionized Water | | | 27.4 |
| Total | | | 100 |

Washing Conditions

Fabrics (2.0 kg of cotton terry towels) were washed at 40° C. in a standard European horizontal axis machine (Miele Novotronic W 900-79 CH). There were dispensed 75 g of freshly prepared liquid detergent at the start of the wash through the detergent drawer. After the wash, fabrics were line-dried overnight before the odor intensity of the cotton towels was evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor.

Results

The results are shown in table 17 below:

TABLE 17

Olfactive performance of microcapsules according to the invention in a concentrated structured liquid detergent

| | Line Drying | |
|---|---|---|
| Perfume Intensity | Before rubbing | After rubbing |
| Structured liquid detergent (no capsules) | 2.52 | 2.78 |
| +0.2% of Capsules B with core oil made of 90% comparative Perfume F and 10% benzyl benzoate | 3.12 | 3.68 |
| +0.2% Capsules B with core oil made of 90% Perfume A and 10% benzyl benzoate | 3.91 | 4.75 |
| +0.07% Capsules B with core oil made of 90% Perfume C and 10% benzyl benzoate | 3.67 | 4.49 |
| +0.07% Capsules B with core oil made of 90% Perfume D and 10% benzyl benzoate | 3.8 | 4.95 |

Conclusion After drying, fabrics which have been washed and conditioned with either capsules deliver a strong perfume boost of dry fabrics. This can be achieved with only 0.07% of capsules loaded with the high impact perfumes C and D or with 0.20% of capsules of perfume A.

Example 16

Olfactive Performance of Microcapsules According to the Invention in a Concentrated Pearly Shampoo Structured Base Formulation:

TABLE 18

Formulation of the structured shampoo

| | Ingredients | % |
|---|---|---|
| A | WATER DEIONISED | 45.97 |
| | EDETA B POWDER (Tetrasodium EDETA) | 0.05 |
| | JAGUAR C14 S (Guar Hydroxypropyltrimonium Chloride) | 0.05 |
| | UCARE POLYMER JR-400 (Polyquaternium-10) | 0.075 |
| B | NAOH SOL. 10% | 0.30 |
| C | SULFETAL LA B-E (Ammonium Lauryl Sulfate) | 34.00 |
| | ZETESOL LA (Ammonium Laureth Sulfate) | 9.25 |
| | TEGOBETAINE F-50 (Cocamidopropyl Betaine) | 2.00 |
| | XIAMETER MEM-1691 (Dimethicone (&) C12-13 Pareth-4 (&) C12-13 Pareth-23 (and) Salicylic Acid) | 2.50 |
| D | CETYL ALCOHOL | 1.20 |
| | COMPERLAN 100 (Cocamide MEA) | 1.50 |
| | CUTINA AGS (Glycol Distearate) | 2.00 |
| E | KATHON CG (Methylchloroisothiazolinone & Methylisothiazolinone) | 0.10 |
| | PANTHENOL 75% | 0.10 |
| | WATER DEIONISED | 0.30 |
| F | SODIUM CHLORIDE 25% | 0.60 |
| | TOTAL: | 100.00 |

Final viscosity is adjusted with 25% NaCl solution.
Viscosity : 1500-2500 cPs (sp 5/50 RPM)
0.7% of fragrance
pH: 5.5-6.0
Shampoo wash protocol
a) Incorporate capsule at the required dosage in the shampoo base
b) Wet the hair swatches under warm water before applying the shampoo per hair swatch (0.1 g of product for 1 g hair)
c) Thoroughly rinse the hair swatches by dipping them 3 times into warm water before rinsing them for 30 seconds under running tap water
d) Squeeze off residual water before air-drying the hair swatches on a drying rack
e) Evaluate after 24 hours, when hair is fully dry Olfactive Performance on 24 h Dry Hair

TABLE 19

Olfactive performance of microcapsules according to the invention in a pearly shampoo

| | After 24 h air Drying | |
|---|---|---|
| Perfume Intensity | Before combing | After combing |
| Isotropic Shampoo (no capsules) | 1.80 | 2.25 |
| +0.8% Capsules C with core oil made of 90% Comparative Perfume F & 10% of a 80/20 mix of benzyl benzoate and phenylethyl phenoxyacetate | 3.8 | 4.9 |

TABLE 19-continued

Olfactive performance of microcapsules according to the invention in a pearly shampoo

|  | After 24 h air Drying | |
|---|---|---|
| Perfume Intensity | Before combing | After combing |
| +0.3% Capsules C with core oil made of 90% Perfume G and 10% of a 80/20 mix of benzyl benzoate and phenylethyl phenoxyacetate | 3.1 | 5.3 |

Conclusion

All hair swatches washed and conditioned with capsules according to the invention do deliver a perfume boost even for a very low dosage. Furthermore, this can be achieved with only 0.3% of capsules C loaded with the high impact perfume G but requires a much higher dosage of 0.8% of capsules with comparative perfume F outside the invention.

Example 17

Olfactive Performance of Microcapsules According to the Invention in a Concentrated Rinse-Off Hair Conditioner Structured Base Formulation:

TABLE 20

Composition of the rinse-off hair conditioner

| | Ingredients | % |
|---|---|---|
| A | WATER DEIONISED | 86.30 |
| | GENAMIN CTAC (Cetrimonium Chloride) | 1.50 |
| | TYLOSE H10 Y G4 (Hydroxyethylcellulose) | 1.50 |
| B | LANETTE O (Cetearyl Alcohol) | 4.00 |
| | ARLACEL 165 (Glyceryl Stearate (and) PEG-100 Stearate) | 2.60 |
| | DIMETHICONE 200 fluid 60000 Cst. | 2.50 |
| | XIAMETER MEM 169 1 (Dimethicone (&) C12-13 Pareth-4 (&) C12-13 Pareth-23 (and) Salicylic Acid) | 1.50 |
| C | KATHON CG (Methylchloroisothiazolinone & Methylisothiazolinone) | 0.10 |
| | TOTAL: | 100.00 |

Procedure:

1/Phase A

2/Phase B: combine and melt all ingredients of phase B at 70-75° C.

3/Keep mixing until cooled down to 40° C. and add phase C while agitating.

Rinse-Off Hair Conditioner Wash Protocol a) Incorporate capsule at the required dosage in the Hair Rinse-off conditioner.
b) Rinse the hair swatches with warm tap water and squeeze out excess water.
c) Apply unperfumed shampoo (0.1 g per 1 g of hair) and wash for 30 sec.
d) Rinse carefully with warm, running tap water and squeeze out excess water.
e) Apply the Hair Rinse-off Conditioner (0.1 g of product per 1 g hair)
f) Thoroughly rinse the hair swatches by dipping them 3 times into warm water before rinsing them for 30 seconds under running tap water
g) Squeeze off residual water before air-drying the hair swatches on a drying rack.
h) Evaluate after 24 hours, when hair is fully dry Results The results are shown in Table 21 below.

TABLE 21

Olfactive performance on 24 h dry hair conditioned with the base above

|  | After 24 h air Drying | |
|---|---|---|
| Perfume Intensity | Before combing | After combing |
| Reference conditioner without capsules | 1.60 | 2.15 |
| +0.8% Capsules C with core oil made of 90% comparative Perfume F and 10% of a 80/20 mix of benzyl benzoate and phenylethyl phenoxyacetate | 4.1 | 6.3 |
| +0.3% Capsules C with core oil made of 90% Perfume G and 10% of a 80/20 mix of benzyl benzoate and phenylethyl phenoxyacetate | 5.0 | 6.5 |

Conclusion

All hair swatches washed and conditioned with capsules according to the invention do deliver a perfume boost even for a very low dosage. This can be achieved with only 0.3% of capsules C loaded with the high impact perfume G but requires a much higher dosage of 0.8% of capsules with comparative perfume F outside the invention.

The invention claimed is:

1. A microcapsule slurry comprising at least one microcapsule having an oil-based core and a polymeric shell, characterized in that the oil-based core comprises:
   25-98 wt % of a perfume oil comprising at least 15 wt % of high impact perfume raw materials having a Log T←4, and
   2-75 wt % of a density balancing material having a density greater than 1.07 g/cm$^3$.

2. The microcapsule slurry according to claim 1, wherein the perfume oil comprises at least 30 wt % of high impact perfume raw materials having a Log T←4.

3. The microcapsule slurry according to claim 1, wherein the polymeric shell is made of a material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum arabic shell wall and mixtures thereof.

4. The microcapsule slurry according to claim 1, wherein the high impact perfume raw materials having a Log T←4 are selected from the group consisting of: (+−)-1-methoxy-3-hexanethiol; 4-(4-hydroxy-1-phenyl)-2-butanone; (+−)-2-(4-methyl-3-cyclohexen-1-yl)-2-propanethiol; 2-methoxy-4-(1-propenyl)-1-phenyl acetate; pyrazobutyle; 3-propylphenol; 1-(3-methyl-1-benzofuran-2-yl)ethanone; 2-(3-phenylpropyl)pyridine; a combination of 1-(3,3-dimethyl-1-cyclohexen-1-yl)-4-penten-1-one and 1-(5,5-dimethyl-1-cyclohexen-1-yl)-4-penten-1-one; 1-(5,5-dimethyl-1-cyclohexen-1-yl)-4-penten-1-one; (3RS,3aRS,6SR,7aSR)-perhydro-3,6-dimethyl-benzofuran-2-one; (+−)-1-(5-ethyl-5-methyl-1-cyclohexen-1-yl)-4-penten-1-one; (1'S,3'R)-methyl-2-[(1',2',2'-trimethylbicyclo[3.1.0 ]hex-3'-yl)methyl]cyclopropyl]methanol; (+−)-3-mercaptohexyl acetate; (2E)-1-(2,6,6-trimethyl-1,3-cyclohexadien-1-yl)-2-buten-1-one; 7-methyl-2H-1,5-benzodioxepin-3(4H)-one; (2E,6Z)-2,6-nonadien-1-ol; (4Z)-4-dodecenal; (+−)-4-hydroxy-2,5-dimethyl-3(2H)-furanone; methyl 2,4-dihydroxy- 3,6-dimethylbenzoate; 3-methylindole; (+−)-perhydro-4alpha,8abeta-dimethyl-4a-naphthalenol; patchoulol; 2-methoxy-4-(1-propenyl)phenol; a combination of (+−)-5,6-dihydro-4-methyl-2-phenyl-2h-pyran and tetrahydro-4-methylene-2-phenyl-2H-pyran; a combination of 4-methylene-2-phenyltetrahydro-2H-pyran and (+−)-4-methyl-2-phenyl-3,6-dihydro-2H-pyran; 4-hydroxy-3-methoxybenzaldehyde; nonylenic aldehyde; 2-methoxy-4-propylphenol; a combination of (2Z)-3-methyl-5-phenyl-2-pentenenitrile and (2E)-3-methyl-5-phenyl-2-pentenenitrile; 1-(spiro[4.5]dec-7-en-7-yl)-4-penten-1-one; 2-methoxynaphthalene; (−)-(3aR,5aS,9aS,9bR)-3a,6,6,9a-tetramethyldodecahydronaphtho[2,1-b]furan; 5-nonanolide; (3aR,5aS,9aS,9bR)-3a,6,6,9a-tetramethyldodecahydronaphtho[2,1-b]furan; 7-isopropyl-2H,4H-1,5-benzodioxepin-3-one; coumarins; 4-methylphenyl isobutyrate; (2E)-1-(2,6,6-trimethyl-1,3-cyclohexadien-1-yl)-2-buten-1-one; beta,2,2,3-tetramethyl-delta-methylene-3-cyclopentene-1-butanol; delta damascone ((2E)-1-[(1RS,2SR)-2,6,6-trimethyl-3-cyclohexen-1-yl]-2-buten-1-one); (+−)-3,6-dihydro-4,6-dimethyl-2-phenyl-2H-pyran; anisaldehyde; paracresol; 3-ethoxy-4-hydroxybenzaldehyde; methyl 2-aminobenzoate; ethyl methylphenylglycidate; octalactone G; ethyl 3-phenyl-2-propenoate; (−)-(2E)-2-ethyl-4-[(1R)-2,2,3-trimethyl-3-cyclopenten-1-yl]-2-buten-1-ol; paracresyl acetate; dodecalactone; tricyclone; (+)-(3R,5Z)-3-methyl-5-cyclopentadecen-1-one; undecalactone; (1R,4R)-8-mercapto-3-p-menthanone; (3S,3aS,6R,7aR)-3,6-dimethylhexahydro-1-benzofuran-2(3H)-one; beta ionone; (+−)-6-pentyltetrahydro-2H-pyran-2-one; (3E,5Z)-1,3,5-undecatriene; a combination of 10-undecenal, (9E)-9-undecenal, and (9Z)-9-undecenal; (Z)-4-decenal; (+−)-ethyl 2-methylpentanoate; 1,2-diallyldisulfane; a combination of (2Z)-2-tridecenenitrile, (3Z)-3-tridecenenitrile; (3E)-3-tridecenenitrile and (2E)-2-tridecenenitrile; (+−)-2-ethyl-4,4-dimethyl-1,3-oxathiane; (+)-(3R,5Z)-3-methyl-5-cyclopentadecen-1-one; 3-(4-tert-butylphenyl)propanal; allyl (cyclohexyloxy)acetate; methylnaphthylketone; a combination of (+−)-(4E)-3-methyl-4-cyclopentadecen-1-one, (+−)-(5E)-3-methyl-5-cyclopentadecen-1-one and (+−)-(5Z)-3-methyl-5-cyclopentadecen-1-one; a combination of cyclopropylmethyl(3Z)-3-hexenoate and cyclopropylmethyl(3E)-3-hexenoate; (4E)-4-methyl-5-(4-methylphenyl)-4-pentenal; (+−)-1-(5-propyl-1,3-benzodioxol-2-yl)ethanone; 4-methyl-2-pentylpyridine; (+−)-(E)-3-methyl-4-(2,6,6-trimethyl-2-cyclohexen-1-yl)-3-buten-2-one; (3aRS,5aSR,9aSR,9bRS)-3a,6,6,9a-tetramethyldodecahydronaphtho[2,1-b]furan; (2S,5R)-5-methyl-2-(2-propanyl) cyclohexanone oxime; 6-hexyltetrahydro-2H-pyran-2-one; (+−)-3-(3-isopropyl-1-phenyl)butanal; a combination of methyl 2-((1RS,2RS)-3-oxo-2-pentylcyclopentyl)acetate and methyl 2-((1RS,2SR)-3-oxo-2-pentylcyclopentyl)acetate; 1-(2,6,6-trimethyl-1-cyclohex-2-enyl)pent-1-en-3-one indol; 7-propyl-2H,4H-1,5-benzodioxepin-3-one; ethyl praline; (4-methylphenoxy)acetaldehyde; ethyl tricyclo[5.2.1.0 (2,6)]decane-2-carboxylate; (+)-(1'S,2S,E)-3,3-dimethyl-5-(2',2',3'-trimethyl-3'-cyclopenten-1'-yl)-4-penten-2-ol; a combination of (2R,4E)-3,3-dimethyl-5-[(1R)-2,2,3-trimethyl-3-cyclopenten-1-yl]-4-penten-2-ol and (2S,4E)-3,3-dimethyl-5-[(1R)-2,2,3-trimethyl-3-cyclopenten-1-yl]-4-penten-2-ol; 8-isopropyl-6-methyl-bicyclo[2.2.2]oct-5-ene-2-carbaldehyde; methylnonylacetaldehyde; 4-formyl-2-methoxyphenyl 2-methylpropanoate; (E)-4-decenal; (+−)-2-ethyl-4-(2,2,3-trimethyl-3-cyclopenten-1-yl)-2-buten-1-ol; a combination of (1R,5R)-4,7,7-trimethyl-6-thiabicyclo[3.2.1]oct-3-ene and (1R,4R,5R)-4,7,7-trimethyl-6-thiabicyclo[3.2.1]octane; (−)-(3R)-3,7-dimethyl-1,6-octadien-3-ol; (E)-3-phenyl-2-propenenitrile; 4-methoxybenzyl acetate; (E)-3-methyl-5-(2,2,3-trimethyl-3-cyclopenten-1-yl)-4-penten-2-ol; allyl(3-methylbutoxy)acetate (A)+, (+−)-allyl (2-methylbutoxy)acetate; (+−)-(2E)-1-(2,6,6-trimethyl-2-cyclohexen-1-yl)-2-buten-1-one; (1E)-1-(2,6,6-trimethyl-1-cyclohexen-1-yl)-1-penten-3-one.

5. The microcapsule slurry according to claim 4, wherein the perfume oil comprises 4-methyl-2-pentylpyridine as high impact perfume raw material.

6. The microcapsule slurry according to claim 1, wherein the density balancing material is chosen from the group consisting of benzyl salicylate, benzyl benzoate, cyclohexyl salicylate, benzyl phenylacetate, phenylethyl phenoxyacetate, triacetin, methyl and ethyl salicylate, benzyl cinnamate, and mixtures thereof.

7. The microcapsule slurry according to claim 1, wherein the oil-based core comprises from 25 wt % to 85 wt % of the perfume oil and from 15 wt % to 75 wt % of the density balancing agent.

8. A microcapsule powder obtained by drying the slurry as defined in claim 1.

9. A perfuming composition comprising
   (i) the perfume microcapsule slurry as defined in claim 1;
   (ii) at least one ingredient selected from the group consisting of a perfumery carrier and a perfuming co-ingredient; and
   (iii) optionally a perfumery adjuvant.

10. A consumer product, in a liquid form, said consumer product comprising the microcapsule slurry as defined in claim 1.

11. A consumer product comprising:
   a) from 2 to 65% by weight, relative to the total weight of the consumer product, of at least one surfactant;
   b) water and/or water-miscible hydrophilic organic solvent(s);
   c) the microcapsule slurry as defined in claim 1; and
   d) optionally non-encapsulated perfume.

12. A liquid transparent isotropic consumer product, in the form of a liquid detergent, a fabric-softener, a liquid perfume booster, a hair care product or a body care product, said product comprising:
   a) from 2 to 65% by weight, relative to the total weight of the consumer product, of at least one surfactant;
   b) water and/or water-miscible hydrophilic organic solvent(s);
   c) the microcapsule slurry as defined in claim 1 in an amount between 0.01 and 0.3%; and
   d) optionally non-encapsulated perfume.

13. A liquid structured consumer product, in the form of a liquid detergent, a fabric-conditioner, a liquid perfume booster, a shampoo, a shower gel, a liquid soap, a rinse-off hair conditioner, or a body lotion comprising:
   a) from 2 to 65% by weight, relative to the total weight of the consumer product, of at least one surfactant;
   b) optionally, a structuring agent, in an amount between 0.05% and 8%;
   c) water or a water-miscible hydrophilic organic solvent;
   d) the microcapsule slurry as defined in claim 1, in an amount from 0.01 to 2.0%; and
   e) optionally non-encapsulated perfume.

14. A powdered or solid consumer product, comprising the microcapsule powder as defined in claim 8.

15. A powdered or a solid consumer product comprising:
   a) from 2 to 65% by weight, relative to the total weight of the consumer product, of at least one surfactant or polyethylene or polypropylene glycol(s) solid at room temperature b) the microcapsule powder as defined in claim 8 in an amount between 0.01 and 2.0%; and c) optionally perfume or perfume powder that is different from the microcapsule powder.

16. The microcapsule slurry according to claim 1, wherein the perfume oil comprises at least 50 wt % of high impact perfume raw materials having a Log T←−4.

17. A consumer product, in a liquid form, in the form of a home care product, a hair care product or a body care product, said consumer product comprising the microcapsule slurry as defined in claim 1.

18. A liquid transparent isotropic consumer product, in the form of a liquid detergent, a fabric-softener, a liquid perfume booster, a hair care product or a body care product, said product comprising:

a) from 2 to 65% by weight, relative to the total weight of the consumer product, of at least one surfactant;

b) water and/or water-miscible hydrophilic organic solvent(s);

c) a perfuming composition as defined in claim 9 in an amount between 0.01 and 0.3%; and d) optionally non-encapsulated perfume.

19. The powdered or solid consumer product of claim 14 in the form of a home care, a body care or a hair care.

20. A powdered or a solid consumer product comprising:

a) from 2 to 65% by weight, relative to the total weight of the consumer product, of at least one surfactant or polyethylene or polypropylene glycol(s) solid at room temperature b) the perfuming composition as defined in claim 9, in an amount between 0.01 and 2.0%; and optionally perfume or perfume powder that is different from the microcapsule powder.

* * * * *